US 9,354,191 B2

(12) United States Patent
Kawaguchi et al.

(10) Patent No.: US 9,354,191 B2
(45) Date of Patent: May 31, 2016

(54) OXYGEN SENSOR CONTROLLING APPARATUS, OXYGEN SENSOR CONTROLLING METHOD AND COMPUTER READABLE RECORDING MEDIUM

(71) Applicant: NGK SPARK PLUG CO., LTD., Nagoya-shi, Aichi (JP)

(72) Inventors: Soichi Kawaguchi, Inazawa (JP); Yoshinori Hibino, Kasugai (JP); Ryosuke Ichida, Komaki (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 329 days.

(21) Appl. No.: 13/942,840

(22) Filed: Jul. 16, 2013

(65) Prior Publication Data
US 2014/0013819 A1 Jan. 16, 2014

(30) Foreign Application Priority Data
Jul. 16, 2012 (JP) .................................. 2012-158226

(51) Int. Cl.
*G01N 27/04* (2006.01)
*G01N 27/409* (2006.01)

(52) U.S. Cl.
CPC .............. *G01N 27/04* (2013.01); *G01N 27/409* (2013.01)

(58) Field of Classification Search
CPC ............ F02D 41/1494; F02D 41/1456; F02D 41/1476; F02D 41/1454; F02D 41/1495; G01N 27/4067; G01N 27/04; G01N 27/4065; G01N 27/409; G01N 27/4175
See application file for complete search history.

(56) References Cited

U.S. PATENT DOCUMENTS

| 5,852,228 A | 12/1998 | Yamashita et al. |
| 5,974,857 A | 11/1999 | Yamashita et al. |
| 6,286,493 B1 * | 9/2001 | Aoki ................... F02D 41/1494 123/690 |
| 6,341,599 B1 | 1/2002 | Hada et al. |
| 2002/0043460 A1 * | 4/2002 | Ikeda ................. G01N 27/4067 204/424 |
| 2002/0060150 A1 * | 5/2002 | Hashimoto .......... G01N 33/007 204/401 |
| 2006/0047468 A1 * | 3/2006 | Aoki ................... F02D 41/1495 702/132 |
| 2012/0131909 A1 | 5/2012 | Maeda |
| 2012/0273369 A1 * | 11/2012 | Kato ................... F02D 41/1454 205/775 |

FOREIGN PATENT DOCUMENTS

| JP | 6-82416 A | 3/1994 |
| JP | 10-26599 A | 1/1998 |
| JP | 2001-74693 A | 3/2001 |
| JP | 2012-117832 A | 6/2012 |

OTHER PUBLICATIONS

Communication dated Jun. 2, 2015 issued by the Japanese Patent Office in counterpart Japanese Patent Application No. 2012-158226.

* cited by examiner

Primary Examiner — Daniel S Larkin
Assistant Examiner — Jamar Ray
(74) Attorney, Agent, or Firm — Sughrue Mion, PLLC

(57) ABSTRACT

An oxygen sensor controlling apparatus includes: a controller configured to obtain a degradation index of a detection element; obtain a sensor output; detect an internal resistance of the detection element by causing a temporary change between electrodes of the detection element; successively obtain a target resistance value corresponding to the internal resistance using a first sensor output that is a value of the sensor output obtained at a time before or after a period when the temporary change occurs and the degradation index; and feedback control energization of the heater so that the internal resistance becomes the target resistance value.

11 Claims, 15 Drawing Sheets

OXYGEN SENSOR CONTROLLING APPARATUS, OXYGEN SENSOR CONTROLLING METHOD AND COMPUTER READABLE RECORDING MEDIUM

CROSS-REFERENCE TO RELATED APPLICATION

This application is based upon and claims the benefit of priority of Japanese Patent Application No. 2012-158226 filed on Jul. 16, 2012, the contents of which are incorporated herein by reference in its entirety.

BACKGROUND

The present invention relates to an oxygen sensor controlling apparatus that controls an oxygen sensor having a characteristic that a sensor output with respect to an air-fuel ratio is rapidly changed between a rich state and a lean state with a theoretical air-fuel ratio being a boundary in response to an oxygen concentration in an exhaust gas of an internal-combustion engine, an oxygen sensor controlling method and a computer readable recording medium.

In the related art, an oxygen sensor that is provided in an exhaust pipe of an internal-combustion engine of a vehicle and detects a rich state and a lean state of an air-fuel ratio in the internal-combustion engine in response to an oxygen concentration in an exhaust gas has been proposed. The oxygen sensor includes a detection element that includes a solid electrolyte such as zirconia as a main body. In such an oxygen sensor, in a case where the oxygen concentration is expressed by an air-fuel ratio of fuel combusted in the internal-combustion engine to air, an output voltage (sensor output) with respect to the air-fuel ratio is rapidly changed in a binary manner with a theoretical air-fuel ratio being a boundary, and thus, by using this phenomenon, it is possible to detect whether the air-fuel ratio of fuel in the internal-combustion engine is on a rich side or a lean side with reference to the theoretical air-fuel ratio. The solid electrolyte that forms the detection element shows excellent oxygen ion conductivity in a high temperature state (activated state) of about 600° C. or higher. Thus, a heater that heats the detection element is provided in the oxygen sensor. Further, by using the phenomenon that element impedance (internal resistance) of the detection element varies according to temperature of the element, a feedback control for energization of the heater is performed so that the element impedance (internal resistance) reaches a target impedance (target resistance) to maintain the detection element at a constant temperature in an activation temperature.

However, in the detection element of such an oxygen sensor, it is known that the element impedance (internal resistance) gradually increases by degradation due to its use or the like. That is, in the detection element after degradation, the element impedance (internal resistance) at the same temperature is relatively high compared with the detection element before degradation. Thus, in a case where the detection element is degraded, if the above-mentioned feedback control of the heater is performed, a control is performed in a direction where the element impedance is decreased, that is, the element temperature is increased to make the element impedance be close to the target impedance. Then, the detection element is excessively heated, and thus, the element temperature rises, which causes a problem that the degradation is further promoted due to the temperature rise.

In order to solve the problem, JP-A-10-26599 discloses an oxygen concentration detection apparatus that includes degradation determination means for determining a degraded state where an element impedance of a detection element is increased and target impedance change means for increasing a target impedance when it is determined that the detection element is in the degraded state. Further, heater-supplied power comparison means for comparing heater-supplied power supplied to a heater and a predetermined determination value is disclosed as a specific example of the degradation determination means.

SUMMARY

As described above, in the oxygen sensor, the internal resistance value of the detection element is increased according to degradation of the detection element. However, it is determined that the internal resistance value of the detection element is influenced by the degradation and is also influenced by a gas atmosphere around the detection element, and specifically, the difference in an air-fuel ratio in an internal-combustion engine, for example. More specifically, if the internal resistance is measured in various sensor output states with respect to the detection element in the degraded state and the relationship between the sensor output and the internal resistance from a lean state to a rich state is expressed by a graph in which a value of the sensor output of the oxygen sensor corresponding to an air-fuel ratio is represented on a transverse axis and a value of the internal resistance of the detection element at a constant element temperature (for example, 700° C.) is represented on a longitudinal axis, respectively, an inverted V shaped graph in which the internal resistance is not constant with respect to the sensor output and a peak of the internal resistance appears in the vicinity of the center of the sensor output is obtained. Further, if the degradation of the detection element continues, the internal resistance is increased and the entire graph described above shifts upward. In addition, the rise of the internal resistance in the vicinity of the peak becomes large and the difference in the internal resistance due to the difference in the sensor output (gas atmosphere) is particularly noticeable. Thus, the inverted V shaped graph has a pointed end shape.

As understood from the above description, in order to maintain the element temperature of the detection element at a constant target temperature (for example, 700° C.) by performing an appropriate feedback control for energization of the heater so that the internal resistance of the detection element reaches a target resistance value, it is necessary to correct the target resistance value according to the degree of degradation of the detection element and the difference in the gas atmosphere (air-fuel ratio, sensor output) when the internal resistance of the detection element is detected.

An object of the invention is to provide an oxygen sensor controlling apparatus that is capable of performing an appropriate energization control for a heater according to the degree of degradation of a detection element and the difference in a gas atmosphere when an internal resistance is detected.

According to an aspect of the present invention, an oxygen sensor controlling apparatus that controls an oxygen sensor that includes: a detection element made of a solid electrolyte and having a pair of electrodes; and a heater configured to heat the detection element, in which the oxygen sensor has a characteristic that a sensor output respect to an air-fuel ratio is rapidly changed between a rich state and a lean state with a theoretical air-fuel ratio being a boundary in response to an oxygen concentration in an exhaust gas of an internal-combustion engine, the oxygen sensor controlling apparatus comprises:

a controller configured to:

obtain a degradation index that indicates a value according to a degree of degradation of the detection element;

obtain the sensor output from the oxygen sensor;

detect an internal resistance of the detection element by causing a temporary change with respect to one of a voltage between the electrodes of the detection element and an electric current that flows between the electrodes;

successively obtain a target resistance value corresponding to the internal resistance using the degradation index and a first sensor output that is a value of the sensor output obtained at a time before or after a period when the temporary change occurs; and feedback-control energization of the heater so that the internal resistance becomes the target resistance value.

As described above, in the oxygen sensor, the internal resistance value of the detection element is influenced by the degree of degradation of the detection element and the gas atmosphere (air-fuel ratio). Here, the air-fuel ratio may be detected by the sensor output (for example, by an output voltage of a sensor in the case of a voltage output type sensor, or by an output current of a sensor in the case of an electric output type sensor).

Here, in this oxygen sensor controlling apparatus, the degradation index that indicates the value according to the degree of degradation of the detection element is obtained to feedback-control the energization of the heater. Further, the target resistance value that is a target of the detected internal resistance is successively obtained using the first sensor output that is the value of the sensor output obtained at the time before or after the period when the temporary change occurs when the internal resistance of the detection element is detected, in addition to the degradation index. That is, the target resistance value is changed according to the degree of degradation (degradation index) and the gas atmosphere (first sensor output) while maintaining the element temperature of the detection element at a constant target temperature. Further, the energization of the heater is feedback-controlled so that the internal resistance becomes the target resistance value.

Thus, it is possible to appropriately perform the energization control for the heater according to the degree of degradation of the detection element (degradation index) and the difference in the gas atmosphere (first sensor output) when the internal resistance is detected.

The degradation index is an index that indicates the value according to the degree of degradation of the detection element, and for example, a value that is changed according to the internal resistance or internal capacitance of the detection element may be used as the degradation index.

Further, the temporary change that occurs between the electrodes of the detection element when the internal resistance is detected may use any one of a voltage change or a current change, and a technique and a circuit configuration of the detection of the internal resistance may be appropriately selected.

Specifically, for example, one electrode of the detection element is connected to a reference electric potential, and the other electrode thereof is connected to a power source voltage through a reference resistor and a switching element. Further, a resistance voltage divider circuit is configured by the detection element and the reference resistor. Then, the switching element is switched from off to on and electric current flows from the power source voltage to the reference resistor and the detection element, to thereby cause the temporary change in the voltage between the electrodes of the detection element. At this time, the variation of voltage due to the temporary change corresponds to a voltage drop that occurs in the internal resistance as the electric current flows in the internal resistance of the detection element. That is, it is possible to detect the internal resistance of the detection element from the voltage variation due to the temporary change. Alternatively, a technique in which a constant current temporarily flows between the electrodes of the detection element to cause a voltage drop in the internal resistance and the variation of voltage due to the temporary change is obtained to detect the internal resistance may be used.

Further, the first sensor output is a value of a sensor output that is obtained at the time before or after the period when the temporary change occurs, that is, at a time that comes before or after the period. Specifically, a value of a sensor output obtained at a time that comes before the period when the temporary change occurs and comes after the previous period, or a value of a sensor output obtained at a time that comes after the period when the temporary change occurs ends and comes before the next period may be used as the value of the sensor output. Here, the first sensor output may be obtained at a time that is close to the period, before or after the period when the temporary change occurs.

When the temporary change occurs in the voltage between the electrodes of the detection element to detect the internal resistance, the voltage between the electrodes of the detection element before the temporary change occurs in the voltage between the electrodes is obtained as a voltage before change. This voltage is a sensor output that indicates an electromotive force of the detection element according to the oxygen concentration. Here, the obtained voltage before change may be commonly used as the first sensor output.

Further, in the above-described oxygen sensor controlling apparatus, the controller may be configured to obtain a reference resistance value corresponding to the degradation index; and correct the reference resistance value according to a value of the first sensor output to obtain the target resistance value.

In this oxygen sensor controlling apparatus, the reference resistance value corresponding to the value of the degradation index is first obtained, and the reference resistance value is corrected according to the value of the first sensor output to obtain the target resistance value. Thus, it is possible to appropriately and easily obtain the target resistance value using the degradation index and the first sensor output.

The reference resistance value is a value of the internal resistance that is to be obtained under the measurement condition that the air-fuel ratio of an exhaust gas has a specific value according to the value of degradation index of the detection element. Here, the reference resistance value is a value that increases as the degradation of the detection element proceeds.

In the above-described oxygen sensor controlling apparatus, the reference resistance value may be corrected using a correction function that uses the first sensor output as a variable, to obtain the target resistance value.

Further, in this oxygen sensor controlling apparatus, the reference resistance value is corrected using the correction function that uses the first sensor output as a variable, to obtain the target resistance value.

Accordingly, it is possible to easily obtain the target resistance value from the reference resistance value.

Further, in the above-described oxygen sensor controlling apparatus, the correction function may be a composite function of a first correction function that regulates a case where the first sensor output is on a lean side with reference to a predetermined threshold output, with respect to the air-fuel ratio, and a second correction function that regulates a case where the first sensor output is on a rich side with reference to the predetermined threshold output, with respect to the air-fuel ratio.

As described above, when the relationship between the sensor output and the internal resistance in the range of the sensor output (air-fuel ratio) from the lean state to the rich state is shown as a graph, it is determined that an inverted V shaped graph that has a peak value of the internal resistance in the vicinity of the center of the sensor output range from the lean side to the rich side is obtained. In this view, when correcting the reference resistance value to obtain an appropriate target resistance value, the correction may be performed using the inverted V shaped relationship.

Thus, in this oxygen sensor controlling apparatus, the correction function is provided as the composite function of the first correction function that regulates a case where the first sensor output is on the lean side with reference to the predetermined threshold output and the second correction function that regulates a case where the first sensor output is on the rich side with reference to the predetermined threshold output.

Thus, it is possible to express the correction function as a composite function of two simple functions. Here, if a threshold output is set to a value of the sensor output where the internal resistance becomes a peak in the above-mentioned graph, the connection of the first correction function and the second correction function at the threshold output becomes excellent, which is preferable.

Further, in the above-described oxygen sensor controlling apparatus, the first correction function may be provided as a linear function that uses the first sensor output as a variable, a first inclination and a first intercept that are an inclination and an intercept of the first correction function may be respectively provided as a function of the reference resistance value, the second correction function may be provided as a linear function that uses the first sensor output as a variable, and a second inclination and a second intercept that are an inclination and an intercept of the second correction function may be respectively provided as a function of the reference resistance value.

As described above, when the relationship between the sensor output (first sensor output) and the internal resistance is shown as a graph in which the transverse axis represents the value of the sensor output (first sensor output) and the longitudinal axis represents the value of the internal resistance, the inverted V shaped graph is obtained, and thus, it is possible to correct the reference resistance value using this relationship to obtain the target resistance value. Here, due to the inverted V shaped graph, when the correction function is expressed as the composite function of the first correction function and the second correction function, by respectively expressing the first correction and the second correction function as a linear function, it is possible to express the correction function as a composite function of simple linear functions.

Further, as described above, as the degradation of the detection element proceeds, the internal resistance is increased and the entire inverted V shaped graph is shifted upward, and the increase in the internal resistance in the vicinity of the peak becomes large and the inverted V shape is changed to a pointed end shape. That is, the inverted V shape is changed in a direction the inclinations of two sides of the inverted V shape are increased. That is, in either the first correction function or the second correction function expressed as the linear function, the inclination and intercept of the linear function are changed according to the degree of degradation of the detection element, that is, the degradation index and the value of the reference resistance value corresponding thereto. Thus, it may be considered that the first inclination and the first intercept in the first correction function and the second inclination and the second intercept in the second correction function are respectively given as a function of the reference resistance value.

Thus, it is possible to appropriately formularize the first correction function and the second correction function, respectively.

Further, in the above-described oxygen sensor controlling apparatus, the first inclination may have a positive value that is increased as the degradation of the detection element proceeds, and the second inclination may have a negative value of which the absolute value is increased as the degradation of the detection element proceeds.

As described above, in the inverted V shaped graph, the value of the sensor output (first sensor output) from the lean state to the rich state is represented on the transverse axis, and the inclinations of two sides of the inverted V shape become large as the degradation of the detection element proceeds.

Accordingly, in this oxygen sensor controlling apparatus, the inclinations of two sides of the inverted V shape are determined on the basis of this relationship. Specifically, the first inclination of the first correction function that regulates a case where the first sensor output is on the lean side with respect to the air-fuel ratio, among the inclinations two sides, has a positive value that increases as the degradation of the detection element proceeds. Further, the second inclination of the second correction function that regulates a case where the first sensor output is on the rich side with respect to the air-fuel ratio has a negative value of which the absolute value increase as the degradation of the detection element proceeds.

Further, in the above-described oxygen sensor controlling apparatus, the first inclination, the first intercept, the second inclination and the second intercept may be respectively provided as a linear function that uses the reference resistance value as a variable or a linear function that uses the natural logarithm of the reference resistance value as a variable.

As described above, the first inclination, the first intercept, the second inclination and the second intercept are respectively given the function of the reference resistance value. Specifically, it is determined that when each function uses the reference resistance value or the natural logarithm of the reference resistance value as a variable, the function may be approximated by its linear function.

Thus, in this oxygen sensor controlling apparatus, using this relationship, the first inclination, the first intercept, the second inclination and the second intercept are respectively given by a linear function that uses the reference resistance value as a variable or a linear function that uses the natural logarithm of the reference resistance value as a variable. Thus, it is possible to easily calculate the first inclination and the first intercept in the first correction function and the second inclination and the second intercept in the second correction function from the reference resistance value, respectively.

Further, in any one of the above-described oxygen sensor controlling apparatus, a value that is changed according to change in an internal capacitance of the detection element depending on the degradation of the detection element may be obtained as the degradation index under the condition that the internal resistance is constant.

With respect to element impedance of the detection element, it may be considered that the internal resistance and the internal capacitance are equivalently connected in parallel. As described above, as the degradation of the detection element proceeds, the internal resistance is relatively increased, and the internal capacitance is also increased. Accordingly, the value that is changed according to change in the internal resistance or the internal capacitance is a value that reflects the degree of degradation of the detection element. Here, when the value that reflects the degree of degradation is obtained, it is preferable to obtain the degree of degradation in a state where a measurement condition is prepared.

Thus, in this oxygen sensor controlling apparatus, the value that is changed according to the change in the internal capacitance due to the degradation of the detection element is obtained as the degradation index under the condition that the internal resistance is constant. Thus, it is possible to obtain an appropriate degradation index.

Here, for example, a time constant of a voltage change that occurs when electric charges accumulated in the internal capacitance of the detection element are self-discharged through the internal resistance of the detection element, or a value that is changed according to the time constant may be used as the value that is changed according to the change in the internal capacitance.

Further, in the above-described oxygen sensor controlling apparatus, the controller may be configured to shift the detection element voltage generated between the electrodes of the detection element from a pre-shift voltage to a post-shift voltage that is different from the pre-shift voltage; return the detection element voltage from the post-shift voltage to the pre-shift voltage by self-discharge due to the internal resistance and the internal capacitance of the detection element, subsequent to the end of a voltage shift period; and obtain, as the degradation index, a value, according to a time constant, of change in the detection element voltage that occurs in a recovery period.

In this oxygen sensor controlling apparatus, the value, according to the time constant, of the change in the detection element voltage that occurs in the recovery period is obtained as the degradation index under the condition that the internal resistance is constant.

Specifically, first, the detection element voltage that occurs between the electrodes of the detection element is shifted from the pre-shift voltage to the post-shift voltage. Then, in the voltage shift period when the voltage shift is performed, electric current flows in the internal resistance and electric charges are accumulated in the internal capacitance of the detection element, by the voltage increased by the voltage shift.

Thereafter, subsequent to the end of the voltage shift period, the detection element voltage returns to the pre-shift voltage from the post-shift voltage. Then, in the recovery period when the detection element voltage returns to the pre-shift voltage from the post-shift voltage, the electric charges accumulated in the internal capacitance of the detection element by the voltage increased by the voltage shift are self-discharged through the internal resistance of the detection element. Thus, the change in the detection element voltage that is approximately exponentially attenuated by the time constant determined by the internal resistance and the internal capacitance of the detection element and returns to the pre-shift voltage from the post-shift voltage occurs between the electrodes of the detection element.

Here, if the detection element is degraded, since the internal capacitance as well as the internal resistance is increased, the time constant determined by the internal resistance and the internal capacitance is increased according to the change in the internal capacitance even under the condition that the internal resistance is constant. Thus, a difference occurs in the type of the exponential change in the detection element voltage in the recovery period, that is, in the time constant according to the degree of degradation (the time constant is increased according to the degradation). Accordingly, by obtaining the value, according to the time constant, of the change in the detection element voltage, it is possible to appropriately obtain the degradation index that indicates the value according to the degree of degradation of the detection element.

Further, in the above-described oxygen sensor controlling apparatus, a 1-2 voltage difference that is a voltage difference between a first voltage that is the detection element voltage in a first detection time in the voltage shift period and a second voltage that is the detection element voltage in a second detection time in the recovery period after the voltage shift period ends may be obtained as the degradation index.

In this oxygen sensor controlling apparatus, the 1-2 voltage difference is obtained as the degradation index.

Thus, it is possible to obtain, as the degradation index, the 1-2 voltage difference that is easily obtained by measuring two voltages of the first voltage at the first detection time in the voltage shift period and the second voltage at the second detection time in the recovery period after the voltage shift period ends. Here, the 1-2 voltage difference is value that is decreased as the degradation of the detection element proceeds.

DESCRIPTION OF EXEMPLARY EMBODIMENTS

Figure 1:
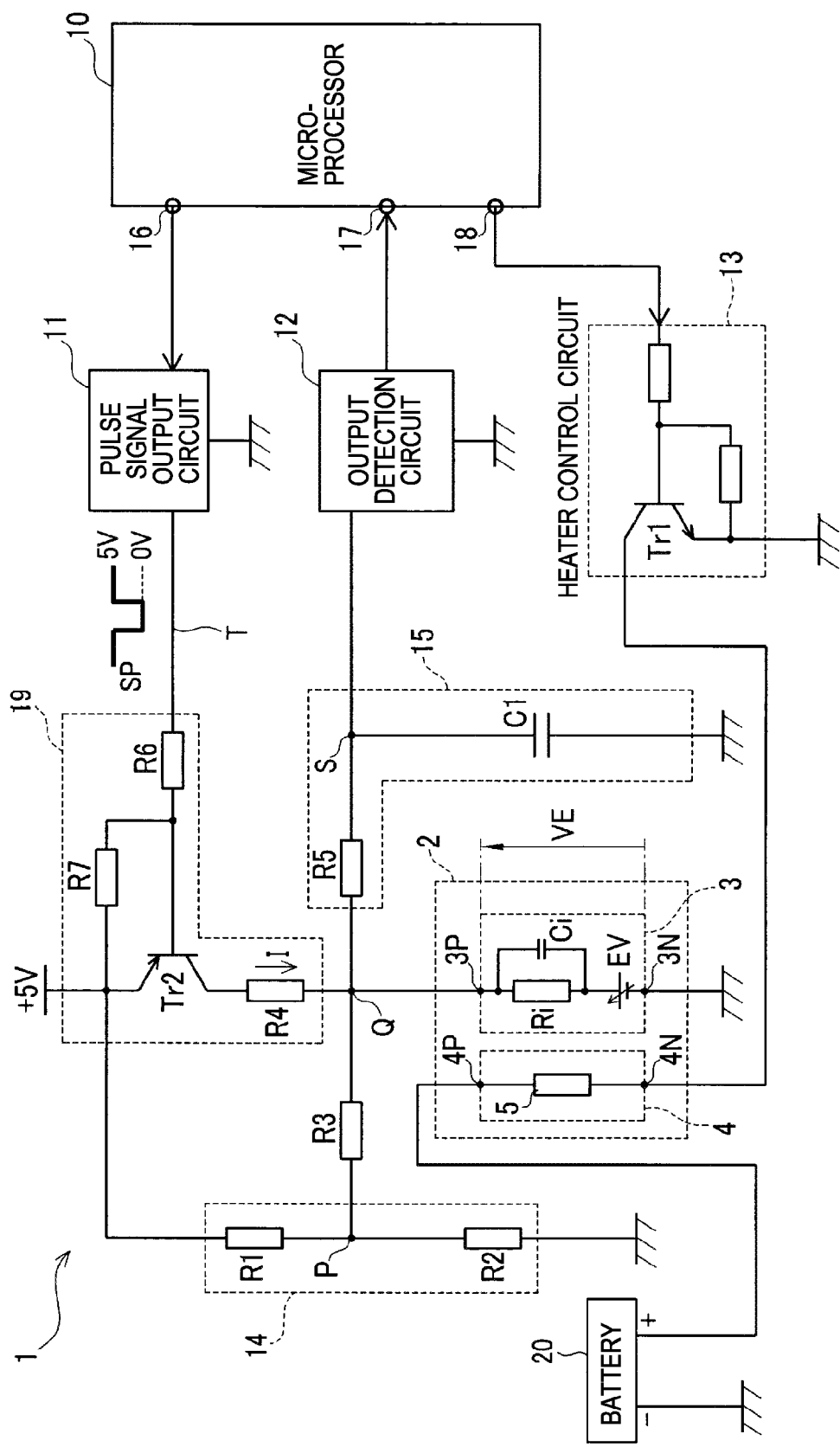
FIG. 1 is a diagram illustrating a schematic configuration that includes a circuit of an oxygen sensor controlling apparatus according to an embodiment of the invention.

Hereinafter, embodiments of the invention will be described referring to the accompanying drawings. FIG. 1 is a diagram illustrating a schematic configuration of an oxygen sensor controlling apparatus 1 according to an embodiment of the invention. The oxygen sensor controlling apparatus 1 is mounted on a vehicle (not shown) that includes an internal-combustion engine (not shown), and is used together with an oxygen sensor 2 to control the oxygen sensor 2. The oxygen sensor 2 is a so-called $\lambda$, sensor that has a characteristic that a sensor output Vout with respect to an air-fuel ratio is rapidly changed between a rich state and a lean state with a theoretical air-fuel ratio being a boundary, and detects whether combustion in the internal-combustion engine is performed on the rich side or the lean side with reference to the theoretical air-fuel ratio.

The oxygen sensor 2 includes a detection element 3 made of a solid electrolyte, and a heater 4 that heats the detection element 3, and the oxygen sensor controlling apparatus 1 controls energization of the heater 4 so that the detection element 3 maintains a constant temperature (for example, 700° C.) in an activation temperature.

First, a configuration of the oxygen sensor 2 will be described. The oxygen sensor 2 includes the detection element 3 that forms a pair of electrodes 3P and 3N using the solid electrolyte that is an oxygen ion conductor that uses zirconia as a main body, and the heater 4 that heats the detection element 3. More specifically, one electrode 3N that is formed on a circumferential surface of the detection element 3 made of the solid electrolyte that forms a bottomed cylindrical shape is exposed to an exhaust gas, and the other electrode 3P that is formed on an inner circumferential surface is exposed to a reference gas (air). Further, the rod-shaped heater 4 is inserted in an internal space of the detection element 3 of the bottomed cylindrical shape, to form the oxygen sensor 2. The detection element 3 made of the solid electrolyte is heated by the heater 4 at an activation temperature that exceeds 600° C. at which the detection elements enters an activated state, which shows excellent oxygen ion conductivity. Further, the detection element 3 generates an electromotive force depending on the oxygen concentration between the electrodes 3P and 3N to output a sensor output Vout. In addition, in the oxygen sensor 2, the energization of the heater 4 is controlled by the oxygen sensor controlling apparatus 1 so that the detection element 3 maintains a constant temperature in the activation temperature.

The heater 4 includes a heat generating resistance body 5 that uses tungsten or platinum as a main body, and terminals 4P and 4N that are connected to the heat generating resistance body 5. One terminal 4P of the heater 4 is connected to a positive pole of a battery 20. A negative pole of the battery 20 is connected to a reference potential that is a chassis GND of the vehicle (hereinafter, referred to as a GND). Further, the other terminal 4N of the heater 4 is connected to a connector output of an NPN transistor Tr1 that is a switching element through a current limiting resistor (not shown) in a heater control circuit 13. Further, an emitter of the transistor Tr1 is connected to the GND, and a base thereof is connected to a PWM output port 18 of the microprocessor 10. Further, the heater 4 is supplied with electricity by a PWM control of the heater control circuit 13, and thus, the detection element 3 is heated. When the detection element 3 is maintained at the constant temperature in the activation temperature, a duty ratio of the PWM control is determined by a PID control or a PI control using the microprocessor 10. The switching element that forms the heater control circuit 13 is not limited to the transistor Tr1, and may be formed using an FET or the like. A voltage of +5 V used in the oxygen sensor controlling apparatus 1 or a voltage of VCC (not shown) of the microprocessor 10 is generated from the battery 20 by a power source circuit (not shown).

The detection element 3 has an internal resistance Ri and has a characteristic in which if the temperature of the detection element 3 is increased, the resistance value is decreased. That is, since there is a predetermined negative correlation between the internal resistance Ri and the element temperature of the detection element 3, by performing a control so that the internal resistance Ri becomes a target resistance value, it is possible to maintain the element temperature at a predetermined temperature.

Further, as described above, the detection element 3 shows the oxygen ion conductivity in the activation temperature to be used as an oxygen concentration cell, and generates an electromotive force EV depending on the oxygen concentration difference between the electrode 3N and the electrode 3P. Accordingly, as shown in FIG. 1, an equivalent circuit of the detection element 3 becomes a circuit in which the battery (oxygen concentration battery) that generates the electromotive force EV and the element impedance are directly connected to each other between the electrodes 3P and 3N. Here, the element impedance may be considered as a parallel connection of the internal resistance Ri that is a pure resistance and an internal capacitance Ci.

However, as described above, the solid electrolyte that forms the detection element 3 has a characteristic in which the internal resistance Ri is reduced according to a temperature increase of the solid electrolyte, but in a non-activated state, when the temperature of the solid electrolyte is low (for example, room temperature), the internal resistance Ri is high, and an approximately insulated state is formed between the electrodes 3P and 3N of the detection element 3. Further, as the temperature of the solid electrolyte is increased, the internal resistance Ri is decreased, and then, in a case where the detection element 3 is activated (in activation), the internal resistance Ri shows a relatively low value. Further, as the temperature of the solid electrolyte is increased, the detection element 3 shows the electromotive force EV depending on the oxygen concentration difference between the electrodes 3P and 3N. The electromotive force EV in activation varies according to the element temperature. Specifically, in a case where the air-fuel ratio of the exhaust gas is on the rich side, the electromotive force EV shows about 900 mV, and in a case where the air-fuel ratio of the exhaust gas is on the lean side, the electromotive force EV shows about 50 mV. Further, the electromotive force EV is rapidly changed with the vicinity of $\lambda=1$ that is the theoretical air-fuel ratio between the rich side and the lean side being a boundary.

Next, the configuration of the oxygen sensor controlling apparatus 1 will be described (see FIG. 1). A bias circuit 14 includes a serial circuit of a resistor R1 and a resistor R2, and distributes a voltage of +5 V into the resistor R1 and the resistor R2. In the present embodiment, specifically, R1=100 k$\Omega$ and R2=10 k$\Omega$, and an electric potential of a point P where the voltage of +5 V is distributed into the resistor R1 and the resistor R2 is set to about 450 mV. The electric potential of the point P is selected to be an approximately intermediate voltage value between about 900 mV on the rich side and about 50 mV on the lean side described above. Further, the electric potential of the point P is connected to the electrode 3P of the detection element 3 at a point Q through a resistor R3 (specifically, R3=10 kΩ) that is the current limiting resistor. Further, the electrode 3N of the detection element 3 is connected to the GND.

Further, the point Q is connected to the voltage of +5 V through a resistor R4 (specifically, R4=8.25 kΩ) and a PNP transistor Tr2 that is a switching element. The switching element is not limited to the transistor Tr2, and may use a switching element such as an SSR or an FET. On the other hand, the point Q is also connected to a low pass filter circuit 15 (specifically, R5=10 kΩ and C1=0.033 µF) for noise removal that includes a resistor R5 and a capacitor C1. A point S that is an output of the low pass filter circuit 15 is connected to an output detection circuit 12. The output detection circuit 12 is installed with a sample hold circuit (not shown), and its output is connected to an A/D input port 17 of the microprocessor 10.

Further, the transistor Tr2 has an emitter connected to +5 V and a collector connected to the resistor R4. Further, a resistor R7 that is a resistor between a base and the emitter and a resistor R6 that is a base input resistor are connected to the base of the transistor Tr2. The resistors R6 and R7, the transistor Tr2 and the resistor R4 form a voltage shift circuit 19. Further, a pulse signal output circuit 11 is connected to a point T that is one end of the resistor R6 in the voltage shift circuit 19. The pulse signal output circuit 11 is connected to an I/O output port 16 of the microprocessor 10, and an output of the I/O output port 16 is output as a pulse signal SP to the point T through the pulse signal output circuit 11. The pulse signal SP normally turns off the transistor Tr2 of the voltage shift circuit 19, and thus, has a voltage of +5 V that is the same as the electric potential of the emitter of the transistor Tr2, which is a rectangular pulse voltage of a negative logic that is temporarily decreased to 0 V only when turning on the transistor Tr2 and returns to +5 V again. Further, a voltage shift (described later) is performed by the pulse signal output circuit 11 that outputs the pulse signal SP and the voltage shift circuit 19.

Specifically, the pulse signal output circuit 11 is a circuit that buffers the output of the I/O output port 16 of the microprocessor 10 in an inverted or non-inverted manner and converts the level of an output voltage from the voltage of VCC of the microprocessor 10 into +5 V, and is configured by a level conversion buffer IC, a transistor or the like. In the present embodiment, the pulse signal output circuit 11 is provided as an inverting buffer circuit in which when the output of the I/O output port 16 is at a level L, the point T that is the output of the pulse signal output circuit 11 becomes +5 V, and when the output of the I/O output port 16 is at a level H, the point T that is the output of the pulse signal output circuit 11 becomes 0V.

As the oxygen sensor controlling apparatus 1 uses such a circuit, it is possible to detect the internal resistance Ri and to obtain a 1-2 voltage difference V1−2 that is a degradation index ID that indicates a value according to the degree of degradation of the detection element 3. Hereinafter, a method of detecting the internal resistance Ri and a method of obtaining the degradation index ID (1-2 voltage difference V1−2) will be specifically described.

Figure 5:
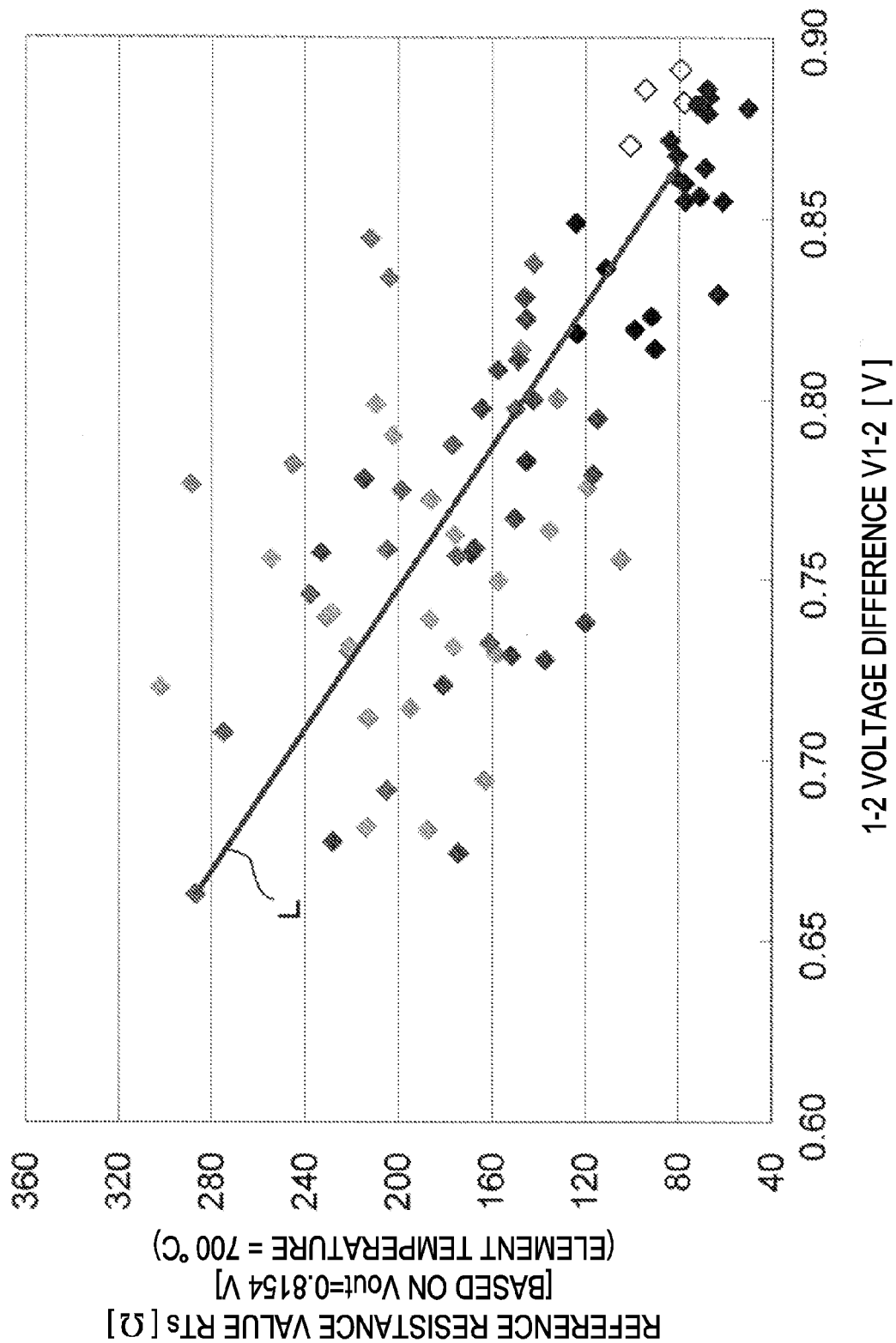
FIG. 5 is a graph illustrating the relationship between a 1-2 voltage difference (degradation index) and a reference resistance value in an oxygen sensor controlling apparatus according to an embodiment of the invention.

First, the method of detecting the internal resistance Ri will be described. In FIG. 1, if the transistor Tr2 is turned off, electric current does not flow into the resistor R4. Further, in activation when the temperature of the solid electrolyte is sufficiently high, for example, as shown in FIG. 5, when the element temperature of the detection element 3 is 700° C., the internal resistance Ri of the detection element 3 becomes about 100Ω or less (in a case where the degradation does not occur) to about 300Ω (in a case where the degradation occurs), which is a sufficiently small value compared with the case of the resistor R2 or the resistor R3. In this activation, the electromotive force EV is also generated in the detection element 3 (about 900 mV on the rich side, and about 50 mV on the lean side). Furthermore, since the internal resistance Ri is sufficiently small, the internal resistance Ri is not almost influenced by the electric current that flows in the resistor R2 or the resistor R3, and the electric potential of the point Q becomes about a value indicated by the electromotive force EV. Further, the electric potential of the point Q is input to the output detection circuit 12 at the point S through the low pass filter circuit 15, and thus, it is possible to detect the electromotive force EV of the detection element 3 by the output detecting circuit 12.

On the other hand, if the transistor Tr2 is turned on, an electric current I flows in the resistor R4. Further, when the detection element 3 is activated, since the internal resistance Ri of the detection element 3 is sufficiently small compared with the resistor R3 or the resistor R2, most of the electric current I flows into the detection element 3. Accordingly, in a state where an excessive electric current that flows in the internal capacitance Ci is converged, the magnitude of the electric current I becomes a value obtained by dividing a value obtained by subtracting the electromotive force EV of the detection element 3 and a voltage (≅0V) between the emitter and the collector of the transistor Tr2 from +5 V by the sum (serially combined resistance) of a value of the resistor R4 and the internal resistance Ri of the detection element 3 (I≅(5−EV)/(R4+Ri)). Accordingly, if the electromotive force EV is constantly maintained while the transistor Tr2 is being turned off and turned on, as the transistor Tr2 is turned on, a detection element voltage VE that is generated between the electrodes 3P and 3N of the detection element 3 while the transistor Tr2 is being turned on is increased by a voltage drop Ri×I generated in the internal resistance Ri, with respect to the detection element voltage VE while the transistor Tr2 is being turned off. That is, a temporary change arises that the detection element voltage VE shifts from a pre-shift voltage VE1 (=EV) to a post-shift voltage VE2 (=EV+Ri×I).

Thus, when a difference (VE2−VE1) between the post-shift voltage VE2 and the pre-shift voltage VE1 is represented as a shift voltage VS, the pre-shift voltage VE1 becomes the electromotive force EV generated by the detection element 3, and the shift voltage VS corresponds to the voltage drop generated as the electric current flows in the internal resistance Ri. That is, the shift voltage Vs is given as follows: VS=Ri×(5−EV)/(R4+Ri). Accordingly, by respectively detecting the pre-shift voltage VE1 (=EV) and the post-shift voltage VE2 (=VE1+Vs=EV+Vs) by the output detecting circuit 12 to obtain the shift voltage VS (voltage variation), it is possible to calculate the internal resistance Ri.

Next, the method of obtaining the degradation index ID (1-2 voltage difference V1−2) will be described. When a period when the voltage shift from the pre-shift voltage VE1 to the post-shift voltage VE2 occurs as the transistor Tr2 is turned on is represented as a voltage shift period TS (see FIG. 2), electric current flows in the internal resistance Ri at the voltage period TS, and thus, the internal capacitance Ci of the detection element 3 is charged (electric charges are accumulated) according to a time constant Ci·Ri.

On the other hand, thereafter, if the transistor Tr2 is turned off and the voltage shift period TS ends, the electric charges accumulated in the internal capacitance Ci are self-discharged through the internal resistance Ri. Thus, the detection element voltage VE is approximately exponentially attenuated according to the time constant Ci·Ri determined by the internal resistance Ri and the internal capacitance Ci of the detection element 3, to thereby cause a change that returns to the pre-shift voltage VE1 from the post-shift voltage VE2 (hereinafter, this period is referred to as a recovery period TK).

However, if the detection element 3 is degraded, the internal resistance Ri of the detection element is relatively increased, and the internal capacitance Ci is also increased. Thus, according to the degree to which the degradation continues, in the change in the detection element voltage VE at the recovery period TK, the time constant Ci·Ri of the change is increased. Accordingly, if the value (1-2 voltage difference V1-2) according to the time constant Ci·Ri of the change in the detection element voltage VE is obtained, it is possible to use the obtained value as the degradation index ID that indicates the degree of degradation of the detection element 3.

When the oxygen concentration is detected, the element temperature is increased up to the activation temperature that exceeds 600° C. in order to cause the detection element 3 to sufficiently function as an oxygen concentration battery for use. For example, when the element temperature of the detection element 3 is about 700° C., the internal resistance Ri of the detection element 3 becomes a small value that is 100Ω or less to about 300Ω, as described above. Furthermore, in the present embodiment, since the resistor R4 is R=8.25 kΩ that is much larger than the above-mentioned value, in a case where the transistor Tr2 is turned on, the shift voltage VS generated by the internal resistance Ri becomes a small value. Thus, the change in the detection element voltage VE that occurs at the recovery period TK is small, and thus, it is difficult to detect the degradation index ID (1-2 voltage difference V1-2) with high accuracy.

However, in a case where the degradation index ID is detected, since it is not necessary to measure the oxygen concentration, it is not necessary to keep the element temperature as high as above. The solid electrolyte that forms the detection element 3 starts showing the oxygen ion conductivity at about 400° C., in the present embodiment, the internal resistance Ri of the detection element 3 when the element temperature is 400° C. becomes about 2560Ω, for example. This value corresponds to a value of about 10 to 30 times the value in the case of 700° C., and corresponds to a value of about ⅓ of the internal resistor R4. In this state, if the degradation index ID is detected, it is possible to increase the shift voltage VS that is proportional to the internal resistance Ri, and to increase the change in the detection element voltage VE that occurs at the recovery period TK. Here, in order to appropriately obtain the degradation index ID for mutual comparison, it is preferable to provide measurement conditions of the degradation index ID.

Thus, in the present embodiment, the degradation index ID when the element temperature is about 400° C. and the internal resistance Ri is 2560Ω is obtained. Specifically, if the operation of the vehicle ends and its engine stops, the energization of the heater 4 of the oxygen sensor 2 is stopped. Then, a predetermined waiting time (for example, 10 minutes) is given to wait for cooling of the detection element 3. Then, the target resistance value is determined so that the internal resistance Ri becomes 2560Ω to control the energization of the heater 4 again, the internal resistance Ri is set to 2560Ω, and then the degradation index ID is detected.

Figure 2:
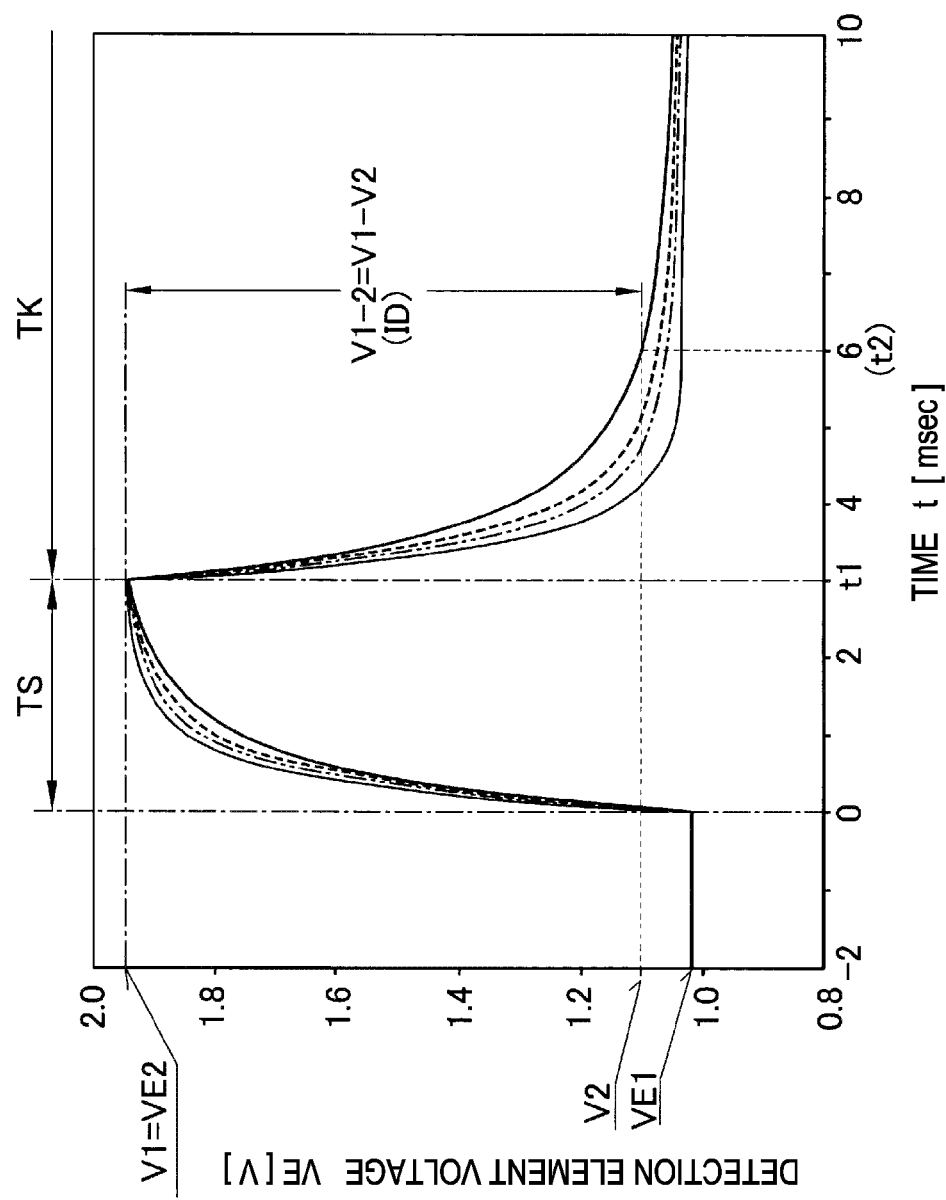
FIG. 2 is a diagram illustrating a change waveform of a detection element voltage when a voltage shift is performed with respect to a detection element by an oxygen sensor controlling apparatus according to an embodiment of the invention.

FIG. 2 shows a change waveform of the detection element voltage VE, at the voltage shift period TS and the recovery period TK, when the voltage shift is performed for the detection element 3 by the oxygen sensor controlling apparatus 1 according to the present embodiment when obtaining the degradation index ID. When obtaining the degradation index ID, the energization of the heater 4 is controlled so that the internal resistance Ri of the detection element 3 becomes 2560Ω.

In FIG. 2, before the voltage shift (before time point t=0), the transistor Tr2 of the voltage shift circuit 19 is turned off, and the detection element voltage VE becomes 1.02V. The detection element voltage VE represents the electromotive force EV of the detection element 3 when the element temperature is about 400° C. This voltage is the pre-shift voltage VE1 (=EV).

Then, at the time point t=0 (beginning time of the voltage shift period TS), if the transistor Tr2 of the voltage shift circuit 19 is turned on, electric current flows into the detection element 3, and a voltage drop occurs in the internal resistance Ri of the detection element 3. Further, the internal capacitance Ci is gradually charged, and the detection element voltage VE rises. In the present embodiment, the voltage shift period TS is set to 3 msec. During the voltage shift period TS, at a first detection time t1 (time point t=t1) that is an ending time thereof, the detection element voltage VE is close to an approximately equilibrium state to be the post-shift voltage VE2. Thus, at the first detection time t1, the detection element voltage VE is detected, which is set as a first voltage V1 (=post-shift voltage VE2).

Under the condition that the internal resistance Ri is controlled to be a constant value (in the present embodiment, Ri=2560Ω), if the voltage shift period TS (in the present embodiment, 3 msec) is sufficiently longer than the time constant Ci·Ri (for example, three or more times the time constant Ci·Ri, the first voltage V1 (post-shift voltage VE2) is converged into a value determined by the internal resistance Ri, and maintains approximately the same value regardless of the degree of degradation.

Then, if the transistor Tr2 is turned off, the voltage shift period TS ends to transit to the recovery period TK when the detection element voltage VE returns to the pre-shift voltage VE1 from the post-shift voltage VE2. As described above, at the recovery period TK, the detection element voltage VE is exponentially attenuated according to the time constant Ci·Ri and returns to the pre-shift voltage VE1 from the post-shift voltage VE2 (see FIG. 2). In the present embodiment, during the recovery period TK, at a second detection time t2 (time point t=t2) when 3 msec elapse after the voltage shift period TS ends, the detection element voltage VE is detected, which is set as a second voltage V2.

Here, as described above, since the internal resistance Ri of the detection element 3 is controlled to be 2560Ω, the post-shift voltage VE2 (the first voltage V1) maintains the approximately the same value regardless of the degree of degradation. On the other hand, the voltage change that occurs at the recovery period TK varies according to the degree of degradation, and the voltage is slowly attenuated as the degradation proceeds. Thus, the second voltage V2 becomes a large value. This is because if the detection element 3 deteriorates, since the internal capacitance Ci as well as the internal resistance Ri are increased, even though the internal resistance Ri is constantly controlled, the time constant Ci·Ri is increased as the degradation proceeds. Thus, the 1-2 voltage difference V1-2 (=V1−V2) that is a difference between the first voltage V1 and the second voltage V2 becomes a small value as the degradation proceeds. Accordingly, the 1-2 voltage difference V1-2 may be used as the degradation index ID that indicates the degree of degradation of the detection element 3.

However, it is determined that the value of the detected internal resistance Ri is affected by the degradation of the detection element 3 and is also affected by the difference in the air-fuel ratio (gas atmosphere).

Figure 4:
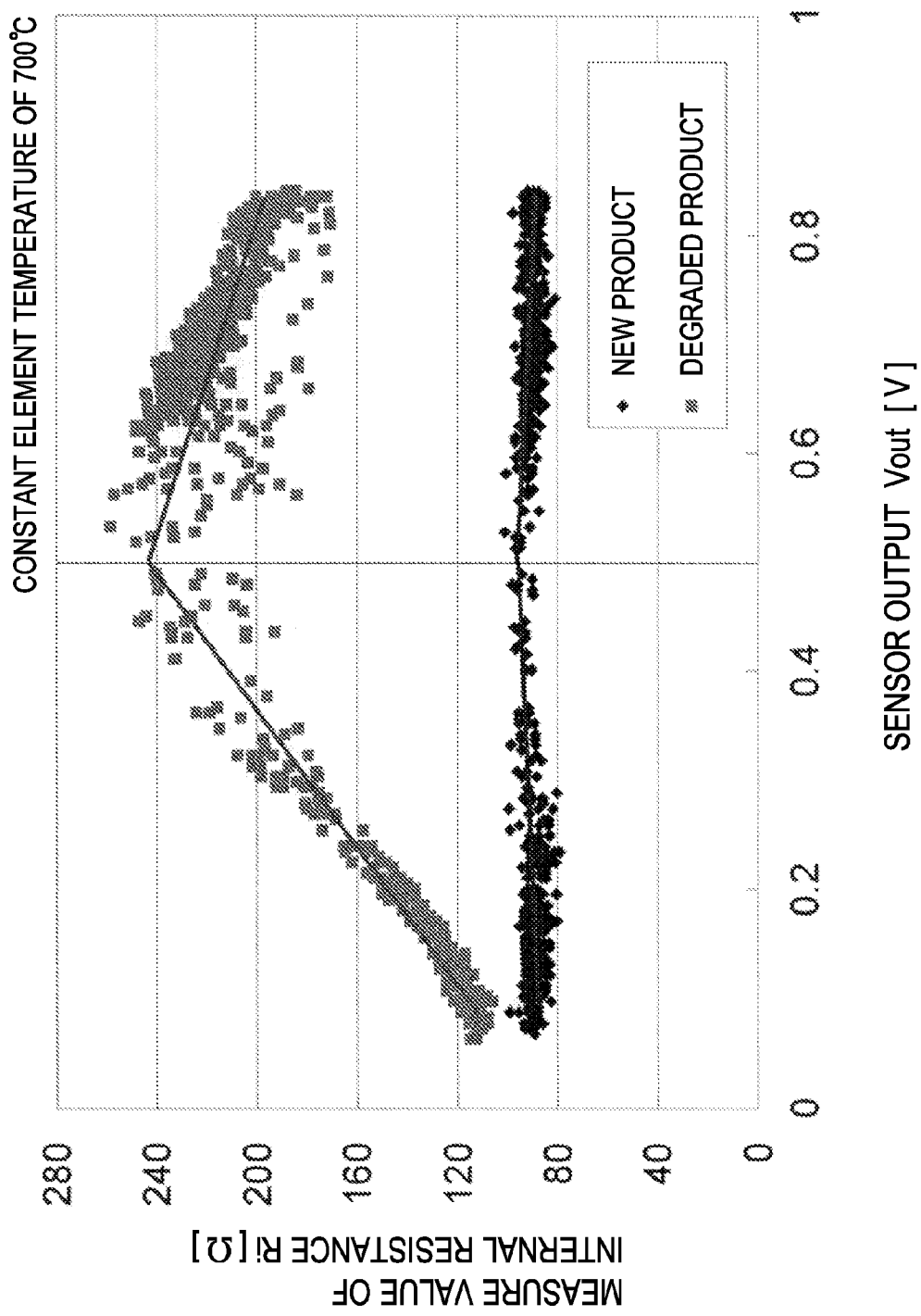
FIG. 4 is a graph illustrating the relationship between a sensor output and an internal resistance in an oxygen sensor controlling apparatus according to an embodiment of the invention.

FIG. 4 is a graph illustrating the relationship between the sensor output Vout and the internal resistance Ri with respect to two oxygen sensors 2 of a product (non-used product) and a degraded product (product returned from the market), in which the transverse axis represents a value of the sensor output Vout of the oxygen sensor 2 corresponding to the air-fuel ratio and the longitudinal axis represents the value of the internal resistance Ri of the detection element 3 in a case where the element temperature is constantly maintained at 700° C. A distribution that is indicated by marks ♦ and is shown in a lower part of the figure represents a measured value of the new product, a distribution that is indicated by marks □ and is shown in an upper part of the figure represents a measured value of the degraded product.

In FIG. 4, a low electric potential side of the sensor output Vout is a lean side with reference to the air-fuel ratio, and a high electric potentials side of the sensor output Vout is a rich side with reference to the air-fuel ratio.

As shown in FIG. 4, the internal resistance Ri is not constant with respect to the sensor output Vout, and the relationship between the sensor output Vout and the internal resistance Ri forms an inverted V shaped graph that has a peak value of the internal resistance Ri in a region where the sensor output Vout is changed from the lean side to the rich side with reference to the air-fuel ratio (in the present embodiment, in the vicinity of Vout=0.5 V).

Further, as understood from comparison of the new product with the degraded product, if the degradation of the detection element 3 proceeds, the internal resistance Ri is increased, an angle formed by the inverted V shape becomes an acute angle, and thus, the entire graph shifts upward.

Further, FIG. 5 is a graph (distribution diagram) illustrating the relationship between the 1-2 voltage difference V1-2 (degradation index ID) and the reference resistance value RTs corresponding thereto. FIG. 5 is a diagram illustrating the relationship between the 1-2 voltage difference V1-2 (degradation index ID) measured with respect to multiple oxygen sensors 2 having different degrees of degradation and the value of the internal resistance Ri measured at the constant element temperature of 700° C. and the sensor output Vout=0.8154 V with respect to the same oxygen sensors. Further, a regression line L is obtained from the distribution of the relationship between the 1-2 voltage difference V1-2 (degradation index ID) and the reference resistance value RTs. That is, the reference resistance value RTs is a target resistance value RT of the internal resistance Ri determined with reference to the sensor output Vout=0.8154 V at the constant element temperature of 700° C. As the degradation of the detection element 3 proceeds from the regression line L and the 1-2 voltage difference V1-2 that is the degradation index ID is decreased (in FIG. 5, the left side), the value of the reference resistance value RTs is increased. In FIG. 5, the 1-2 voltage difference V1-2 on the transverse axis is measured in a state where the internal resistance Ri is controlled to be 2560Ω as described above, and is different in measurement condition from the value of the internal resistance Ri on the longitudinal axis at the constant element temperature of 700° C.

Thus, if the reference resistance value RTs is used, it is possible to perform the energization of the heater 4 according to the degree of degradation of the detection element 3. Here, as shown in FIG. 4, the value of the internal resistance Ri is changed according to the degree of degradation of the detection element 3 and is also changed according to the sensor output Vout (gas atmosphere). Thus, in order to appropriately feedback-control the energization of the heater 4, it is necessary to consider the degree of degradation of the detection element 3 and the difference in the gas atmosphere when the internal resistance Ri is detected.

Thus, in the oxygen sensor controlling apparatus 1 of the present embodiment, when the energization of the heater 4 is feedback-controlled, using the reference resistance value RTs obtained from the 1-2 voltage difference V1-2 (degradation index ID) and a first sensor output Vo1 that is the value of the sensor output Vout obtained at a time before a period when a temporary change occurs in the detection element voltage VE between the electrodes 3P and 3N of the detection element 3 (specifically, the value immediately before the temporary change occurs in the detection element voltage VE), the reference resistance value RTs is corrected according to the value of the first sensor output Vo1 to obtain the target resistance value RT of the internal resistance Ri. Further, the energization of the heater 4 is feedback-controlled so that the detected internal resistance Ri becomes the target resistance value RT.

Figure 3:
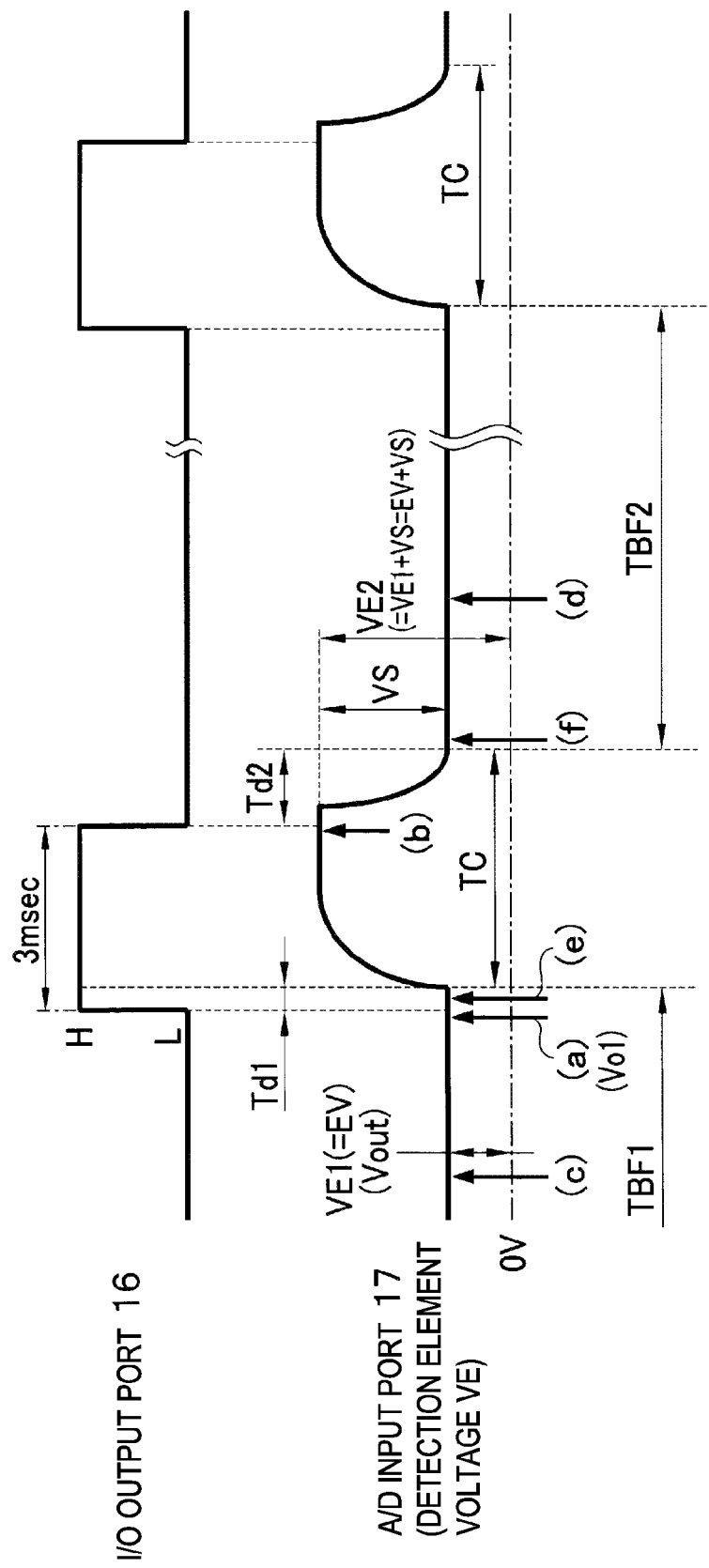
FIG. 3 is a timing chart illustrating an internal resistance detecting operation in an oxygen sensor controlling apparatus according to an embodiment of the invention.

FIG. 3 is a timing chart illustrating the detection operation of the internal resistance Ri. As described above, in order to detect the internal resistance Ri, by causing the temporal change in which the detection element voltage VE between the electrodes 3P and 3N of the detection element 3 shifts from the pre-shift voltage VE1 to the post-shift voltage VE2, the shift voltage VS that is the difference (VE2−VE1) is obtained. Specifically, by changing the output of the I/O output port 16 from a low level to a high level, the transistor Tr2 of the voltage shift circuit 19 is temporarily turned on. Then, since the electric current I flows in the detection element 3, the detection element voltage VE that is input to the A/D input port 17 through the output detection circuit 12 is temporarily changed during a period TC.

Thus, in the present embodiment, in order to detect the internal resistance Ri, first, immediately before the detection element voltage VE rises according to turning on of the transistor Tr2 (time (a) in FIG. 3), the pre-shift voltage VE1 (=EV) is obtained.

Then, after a predetermined time elapses after the transistor Tr2 is turned on (in the present embodiment, after 3 msec), before the transistor Tr2 is turned off again (time (b) in FIG. 3), the post-shift voltage VE2 (=VE1+VS=EV+VS) is obtained. Thus, it is possible to obtain the shift voltage VS (variation of voltage (=VE2−VE1)), and to detect the internal resistance Ri.

However, the pre-shift voltage VE1 (=EV) before the detection element voltage VE rises according to turning on of the transistor Tr2 is also the sensor output Vout indicating the electromotive force EV depending on the oxygen concentration. Thus, in the present embodiment, before the detection element voltage VE rises, for example, the value of the pre-shift value VE1 (=sensor output Vout) obtained immediately before the period TC when the temporary change occurs between the electrodes 3P and 3N of the detection element 3 (time (a) in FIG. 3) is used as the above-mentioned first sensor output Vo1.

As the first sensor output Vout1, the value of the sensor output obtained at a time before or after the period TC when the temporary change occurs, that is, at a time that comes before or after the period TC may be used, and the value is not limited to the value of the pre-shift voltage VE1 obtained immediately before the period TC as in the present embodiment. Specifically, an arbitrary time (for example, time (c) in FIG. 3) during a period TBF1 that comes after the previous period TC and comes before the period TC, or an arbitrary time (for example, time (d) in FIG. 3) during a period TBF2 that comes before the next period TC and comes after the period TC, or the like may be considered, and the value of the sensor output Vout obtained within the period TBF1 or TBF2 before and after the period TC may be used. Here, it is preferable that a time close to the period TC be selected in the period TBF1 or TBF2.

Further, between the output of the I/O output port 16 for tuning on and off the transistor Tr2 and the period TC when the temporary change occurs in the detection element voltage VE in reality, a start delay time Td1 occurs at a starting time, and an end delay time Td2 occurs at an ending time, due to the circuit delay or the internal capacitance Ci of the detection element 3.

Thus, for example, even after the output of the I/O output port 16 for turning on the transistor Tr2 is set to the high level, within the start delay time Td1 (time (e) in FIG. 3), it is possible to obtain the first sensor output Vo1.

Further, after the output of the I/O output port 16 is switched to the low level for turning off the transistor Tr2, and immediately after the period TC ends after the elapse of the end delay time Td2, for example, at a time (f) in FIG. 3, it is possible to obtain the first sensor output Vo1.

Figure 6:
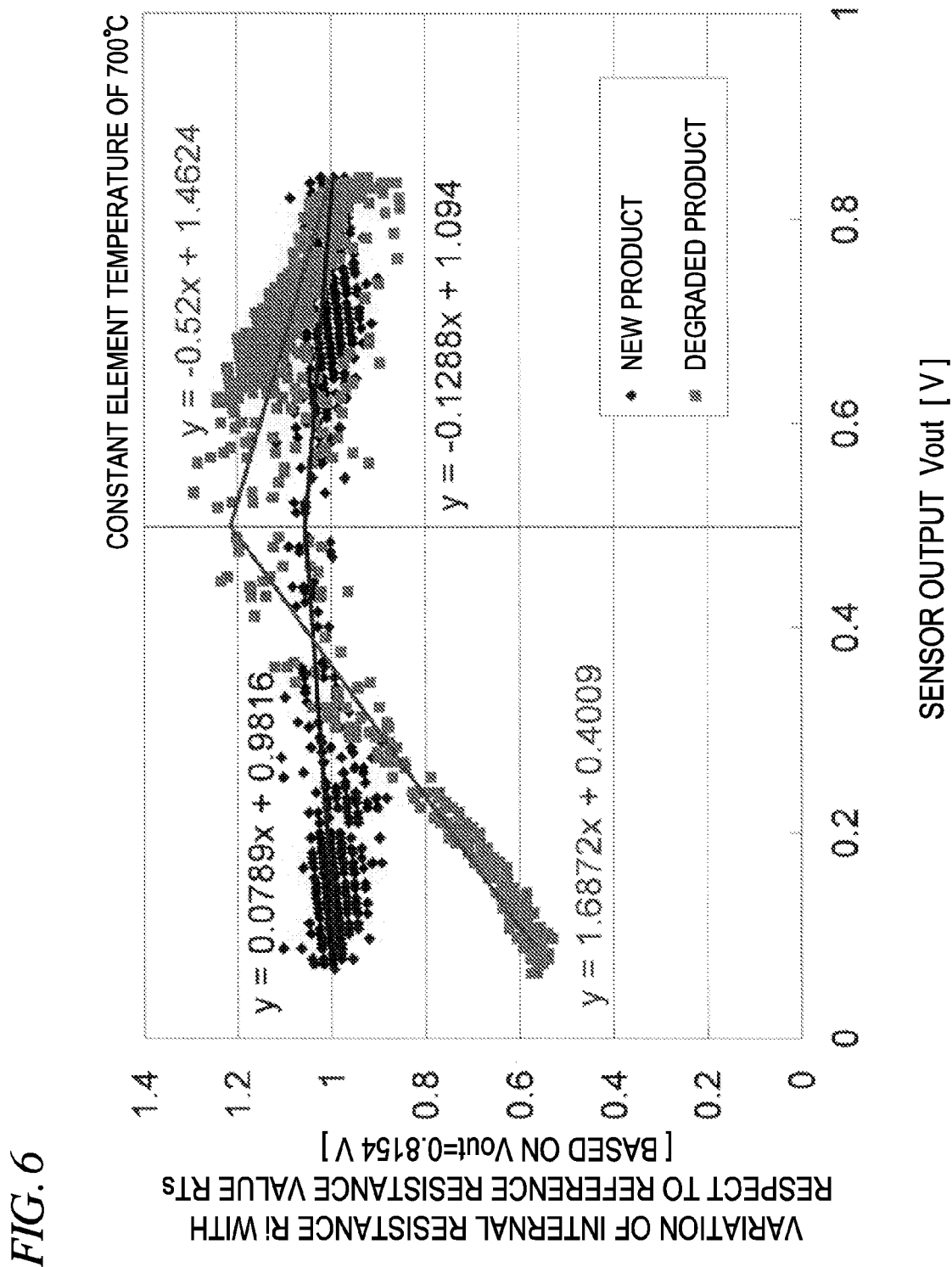
FIG. 6 is a graph illustrating the relationship between a sensor output and variation in an internal resistance with respect to a reference resistance value in an oxygen sensor controlling apparatus according to an embodiment of the invention.
Figure 7:
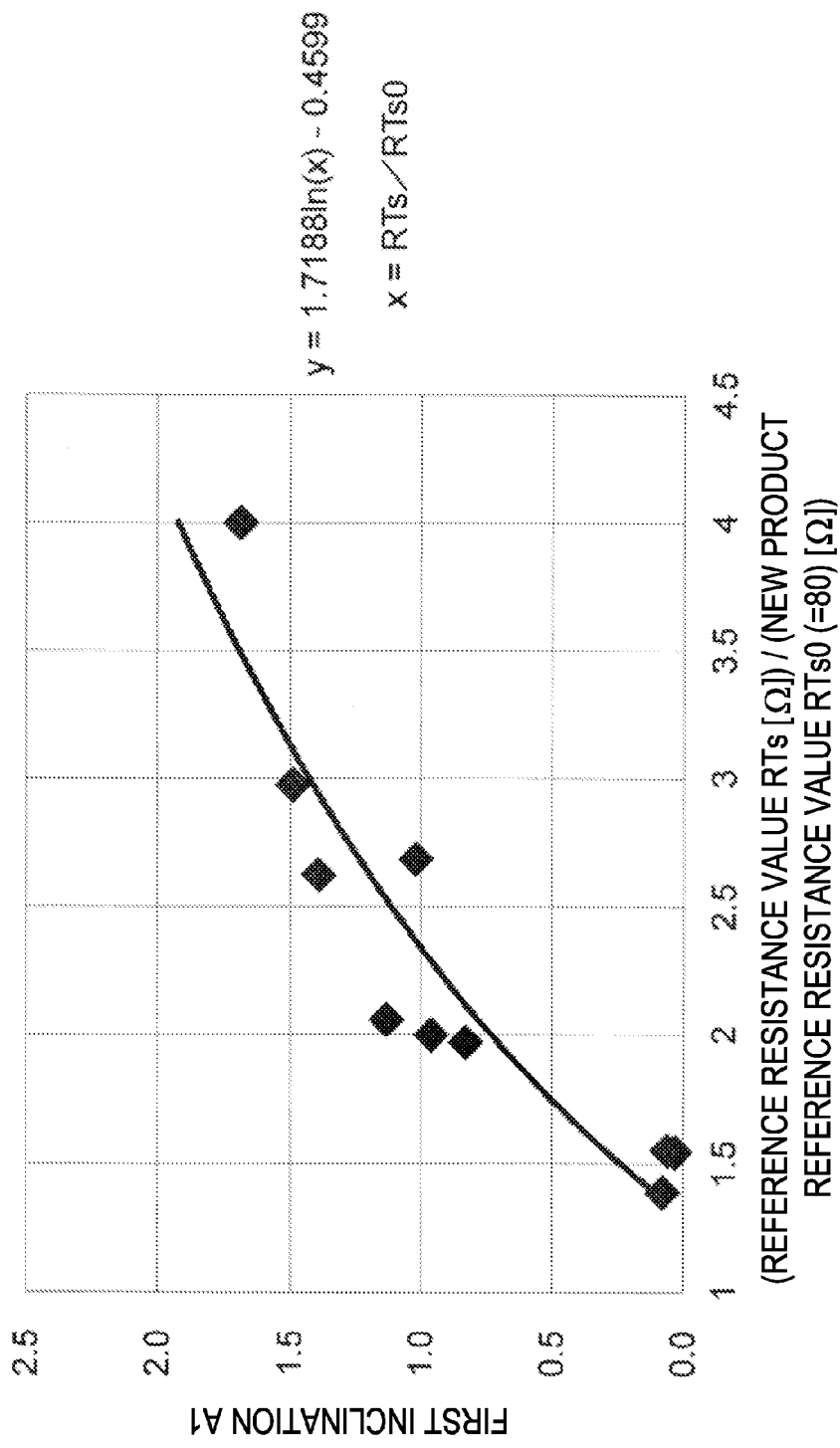
FIG. 7 is a graph illustrating the correlation between a reference resistance value and a first inclination in a first correction function.
Figure 8:
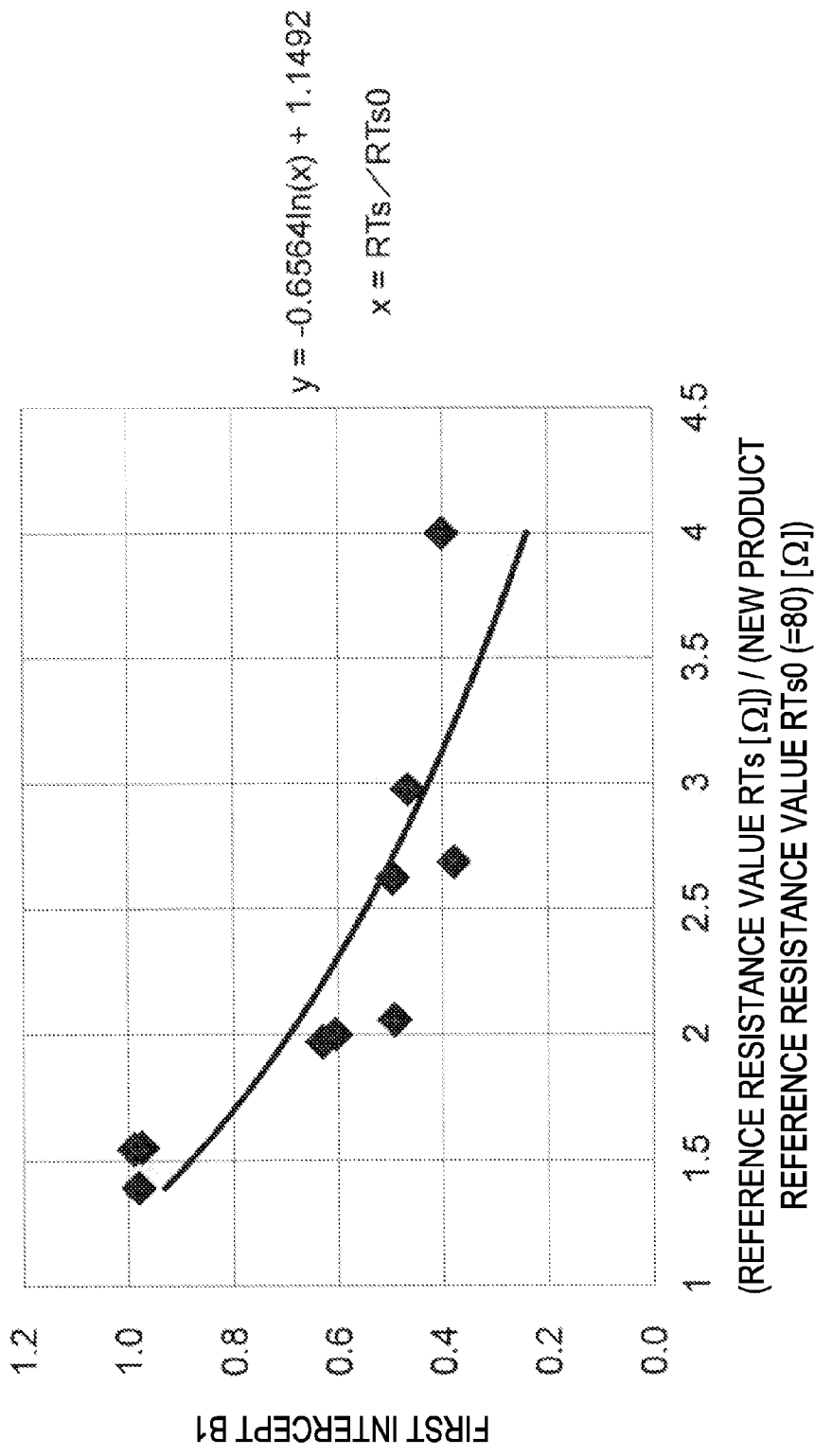
FIG. 8 is a graph illustrating the correlation between the reference resistance value and a first intercept in the first correction function.
Figure 9:
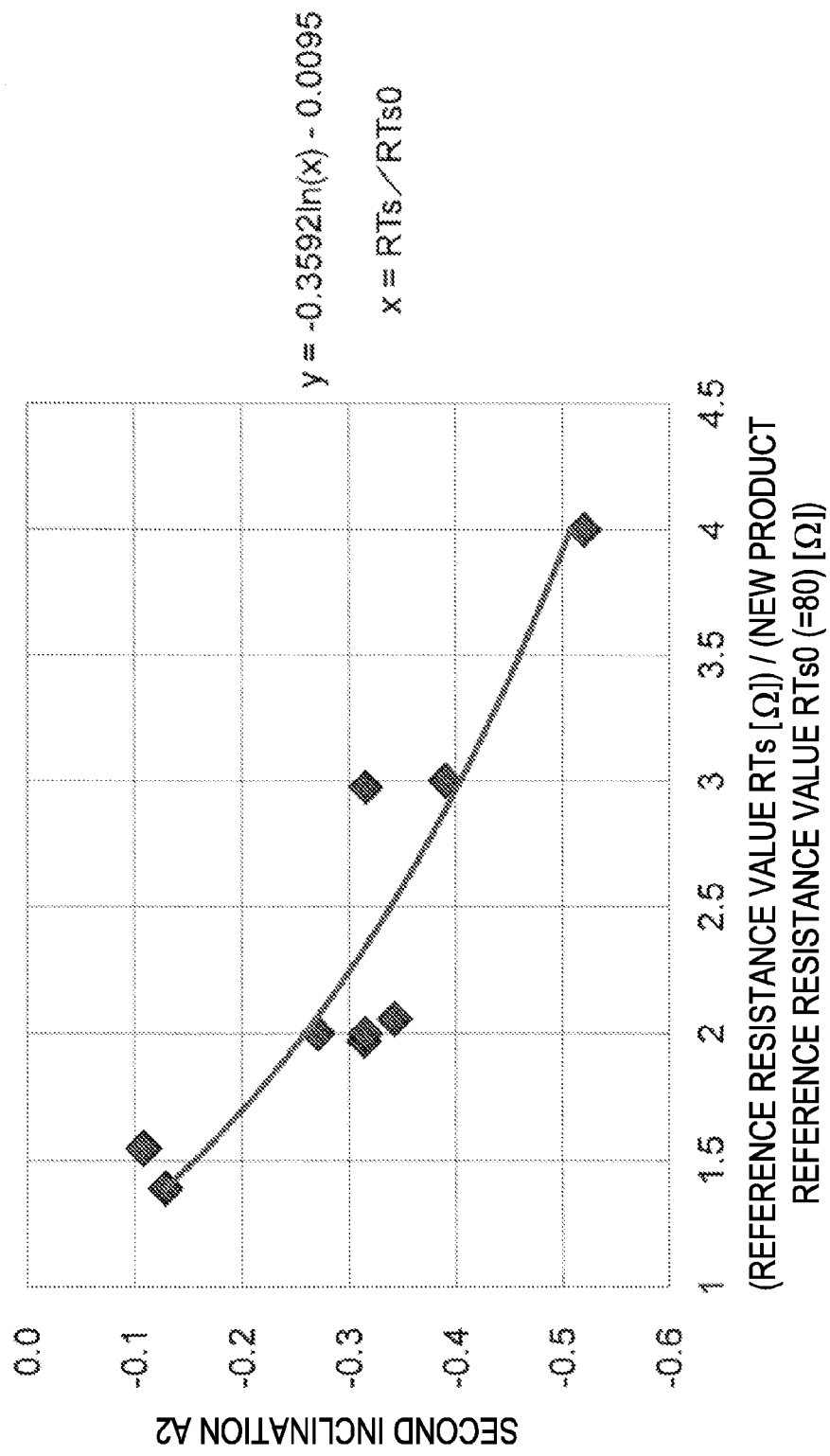
FIG. 9 is a graph illustrating the correlation between a reference resistance value and a second inclination in a second correction function.
Figure 10:
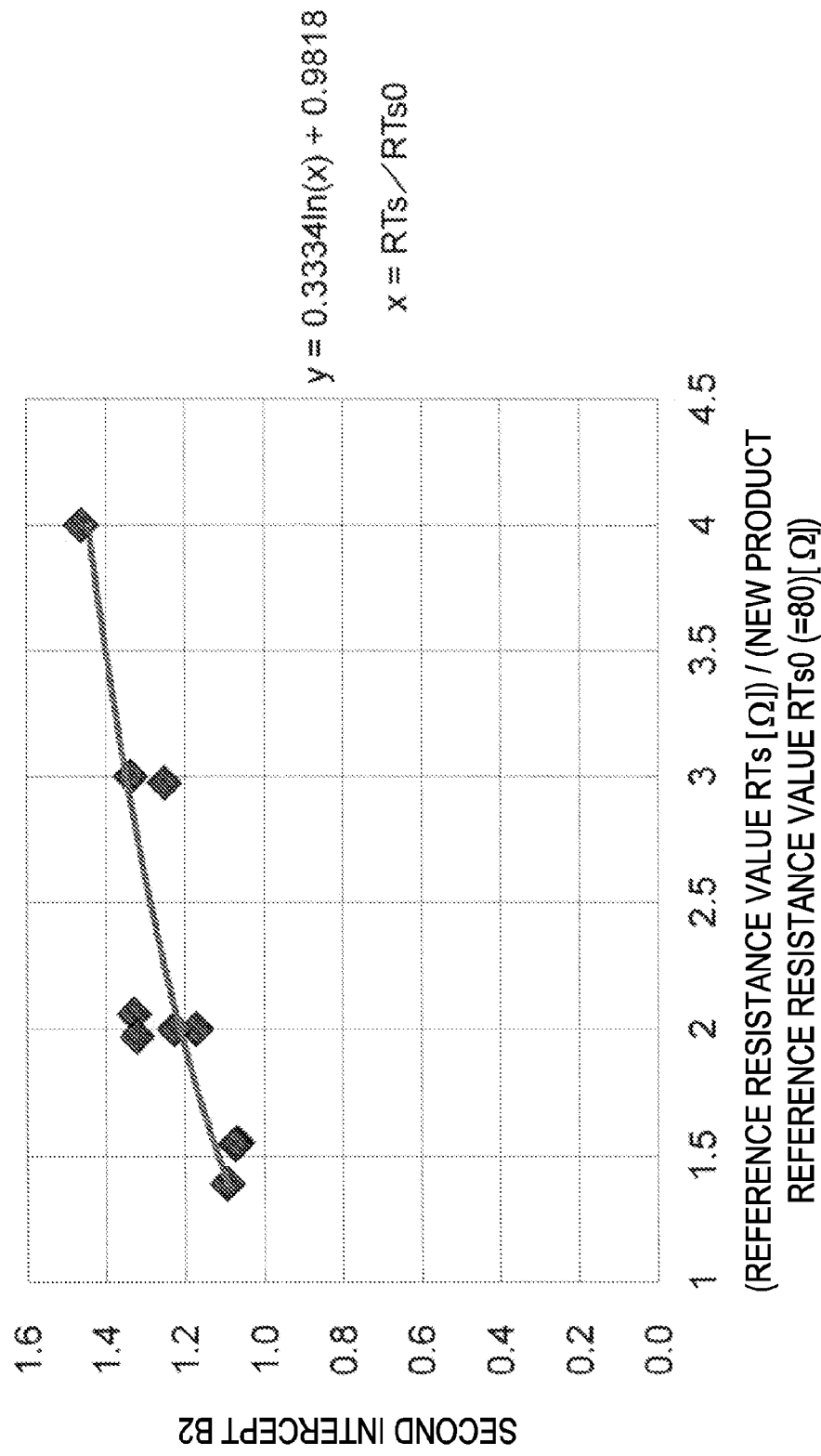
FIG. 10 is a graph illustrating the correlation between the reference resistance value and a second intercept in the second correction function.

Next, the method of obtaining the target resistance value RT will be described. FIG. 6 is a graph that represents a value of the sensor output Vout on the transverse axis and represents the variation of the internal resistance Ri with respect to the reference resistance value RTs (with reference to the sensor output Vout of 0.8154V) on the longitudinal axis, with respect to two oxygen sensors 2 of a new product and a degraded product, on the basis of the graph in FIG. 4.

In FIG. 6, respective inverted V shaped graphs of the new product (marks ♦) and the degraded product (marks ■) may be divided for consideration into a lean side where the sensor output Vout becomes a low electric potential side and a rich side where the sensor output Vout becomes a high electric potential side with a peak value of the internal resistance Ri in the vicinity of a sensor output Vout of 0.5 V being a boundary.

Thus, when the reference resistance value RTs is corrected according to the value of the first sensor output Vo1 to obtain the target resistance value RT, the reference resistance value RTs and the target resistance value RT are formularized into a functional relation, and this function is represented as a correction function fn. Further, the sensor output Vout when the internal resistance Ri represents the peak value is determined as a threshold output Vth (in the present embodiment, Vth is about 0.5 V). Then, the correction function fn may be considered as a composite function of a first correction function fn1 that regulates a case where the first sensor output Vo1 is on the lean side with reference to the threshold output Vth and a second correction function fn2 that regulates a case where the first sensor output Vo1 is on the rich side with reference to the threshold output Vth.

Further, as shown in FIG. 6, the first correction function fn1 and the second correction function fn2 may be expressed as a linear function that uses the first sensor output Vo1 as a variable, by using a regression line of the respective measurement points of marks ♦ or ■. Further, as understood from comparison of the new product with the degraded product, if the degradation of the detection element 3 proceeds, the variation of the internal resistance Ri with respect to the sensor output Vout is increased, and thus, an angle formed by the inverted V shape becomes an acute angle. Accordingly, it may be considered that an inclination and an intercept of the linear function vary according to the degree of degradation of the detection element 3, in the first correction function fn1 and the second correction function fn2.

Thus, when the inclination of the first correction function fn1 is represented as a first inclination A1 and the intercept thereof is represented as a first intercept B1, the first inclination A1 and the first intercept B1 are given as a function of the reference resistance value RTs.

Further, similarly, if the inclination of the second correction element fn2 is represented as a second inclination A2 and the intercept thereof is represented as a second intercept B2, the second inclination A2 and the second intercept B2 are given as a function of the reference resistance value RTs.

Here, the first inclination A1 is a positive value that is increased as the degradation of the detection element 3 proceeds. On the other hand, the second inclination A2 is a negative value of which the absolute value is increased as the degradation of the detection element 3 proceeds.

Further, it is determined that it is preferable to assign the regression formula as a linear function that uses the natural logarithm of the reference resistance value RTs as a variable, in consideration of the relationship with the reference resistance value RTs with respect to the first inclination A1, the first intercept B1, the second inclination A2 and the second intercept B2 (hereinafter, the natural logarithm is expressed as ln).

Specifically, in the present embodiment, the first inclination A1, the first intercept B1, the second inclination A2 and the second intercept B2 are respectively given by the following formulas (see FIGS. 7 to 10).

$$\text{First inclination } A1 = 1.7188 \ln(x) - 0.4599 \quad \text{(Formula 1)}$$

$$\text{First intercept } B1 = -0.6564 \ln(x) + 1.1492 \quad \text{(Formula 2)}$$

$$\text{Second inclination } A2 = -0.3592 \ln(x) - 0.0095 \quad \text{(Formula 3)}$$

$$\text{Second intercept } B2 = 0.3334 \ln(x) + 0.9818 \quad \text{(Formula 4)}$$

Here, x is reference resistance value RTs/new product reference resistance value RTso (=80Ω).

Here, instead of using a natural logarithm (ln(RTs)) of the reference resistance value RTs, in FIG. 5, by using the reference resistance value RTs that is 80Ω (longitudinal axis) as a new product reference resistance value RTso and by using a natural logarithm (ln(x)) of the ratio x (=reference resistance value RTs/new product reference resistance value RTso) of the reference resistance value RTs to the new product reference resistance value RTso (=80Ω), Formula 1 to Formula 4 are expressed. Formula 1 to Formula 4 may be expressed as a linear function that uses the natural logarithm (ln(RTs)) of the reference resistance value RTs as a variable, using the following Formula 5.

$$\begin{aligned} fn2 &= A2 \times Vo1 + B2 \quad &\text{(Formula 7)} \\ &= (-0.3592 \ln(x) - 0.0095) \times Vo1 + \\ &\quad (0.3334 \ln(x) + 0.9818) \end{aligned}$$

As described above, the first correction function fn1 is given by the following formula.

$$\begin{aligned} \ln(x) &= \ln(RTs/RTso) \quad &\text{(Formula 5)} \\ &= \ln(RTs) - \ln(RTso) \\ &= \ln(RTs) - 4.3820 \end{aligned}$$

Further, the second correction function fn2 is given by the following formula.

$$fn1 = A1 \times Vo1 + B1 \quad \text{(Formula 6)}$$
$$= (1.7188 \ln(x) - 0.4599) \times Vo1 +$$
$$(-0.6564 \ln(x) + 1.1492)$$

Accordingly, in the oxygen sensor controlling apparatus 1 of the present embodiment, by using the first correction function fn1 and the second correction function fn2, an appropriate target resistance value RT is obtained from the first sensor output Vo1 and the reference resistance value RTs corresponding to the 1-2 voltage difference V1-2 (degradation index ID), to thereby make it possible to perform an appropriate feedback-control for the internal resistance Ri.

Next, in the oxygen sensor controlling apparatus 1 according to the present embodiment, the operation of the microprocessor 10 will be described referring to the flowchart in FIG. 11.

Figure 11:
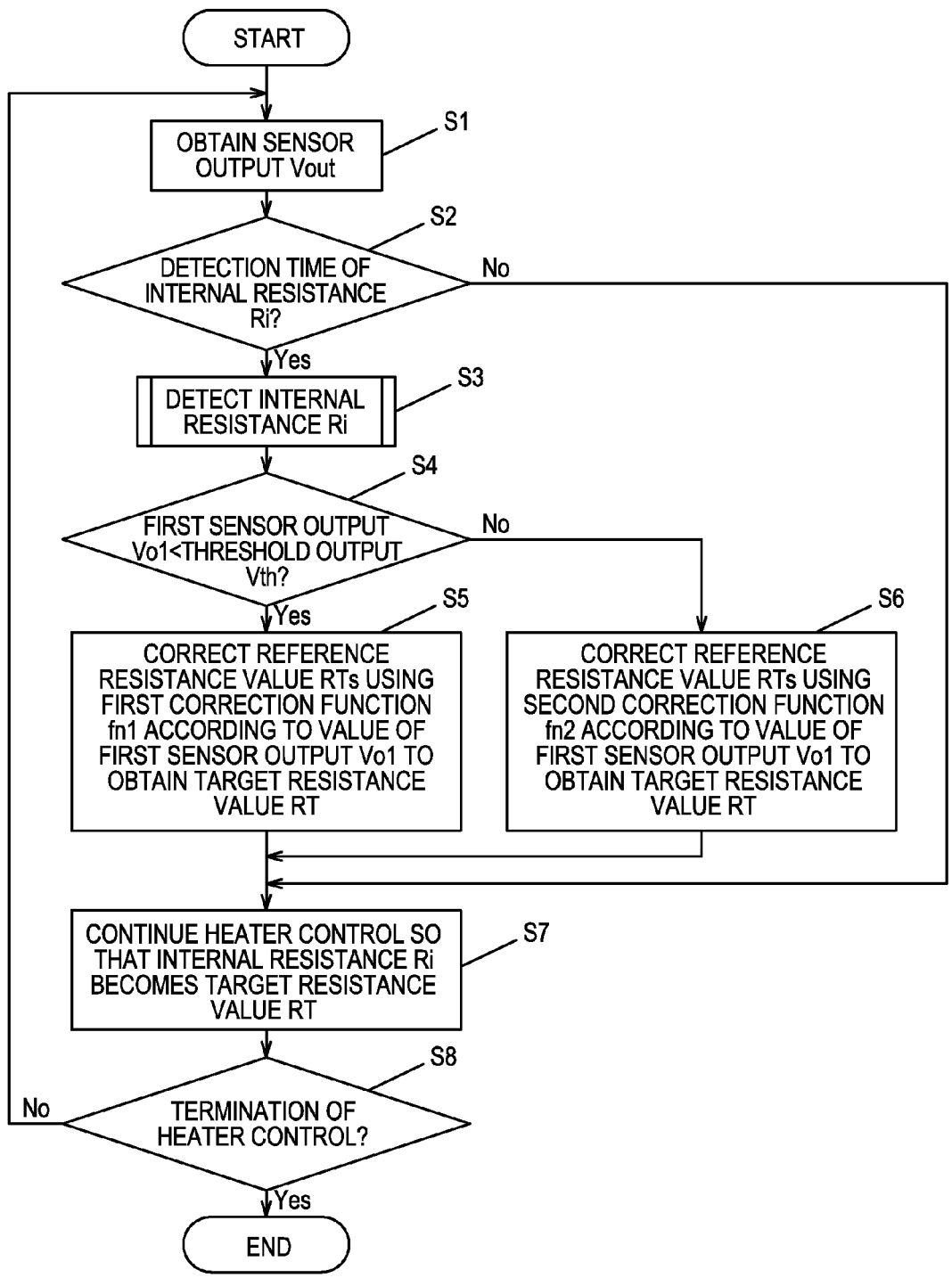
FIG. 11 is a flowchart illustrating a process operation of a microprocessor in an oxygen sensor controlling apparatus according to an embodiment of the invention.

A control program shown in FIG. 11 is a program that is stored in a memory and is called for execution from a main routine that is executed by the microprocessor 10, which includes obtainment of the sensor output Vout, and also includes detection of the internal resistance Ri using an internal resistance detection routine, energization control for the heater 4 and obtainment of the target resistance value RT used therein to be described later.

First, the sensor output Vout of the oxygen sensor 2 is obtained every 10 msec, in step S1. As described above, the oxygen sensor controlling apparatus 1 has a characteristic that the sensor output Vout is rapidly changed between a rich state and a lean state with a theoretical air-fuel ratio being a boundary when the detection element 3 reaches the activation temperature, and the sensor output Vout is about 0.05 V in the lean state, and is about 0.9 V in the rich state. The air-fuel ratio is controlled according to the sensor output Vout.

Then, in step S2, it is determined whether it is a detection time of the internal resistance Ri. Since the detection of the internal resistance Ri is performed at a cycle (500 msec) longer than an obtaining cycle (10 msec) of the sensor output Vout, it is determined in step S2 whether the detection time comes. Further, if the detection time does not come (No), the procedure goes to step S7, and the energization control for the heater 4 is performed. On the other hand, if the detection time comes (Yes), the procedure goes to step S3.

In step S3, by executing the internal resistance detection routine to be described later (see FIG. 12), the shift voltage VS (voltage variation) is obtained by causing a temporary change in the detection element voltage VE between the electrodes 3P and 3N of the detection element 3 using the pulse signal output circuit 11, the voltage shift circuit 19, the low pass filter 15 and the output detection circuit 12, to thereby detect the internal resistance Ri of the detection element 3. Further, in step S31 to be described later in the internal resistance detection routine of step S3, the first sensor output Vo1 is obtained. Specifically, since the pre-shift voltage VE1 obtained in step S31 when the internal resistance Ri is detected is also the sensor output Vout (=EV), this value is commonly used as the first sensor output Vo1.

In the present embodiment, the pre-shift voltage VE1 obtained in step S31 is commonly used as the first sensor output Vo1, but the sensor output Vout that is previously obtained in step S1, instead of the pre-shift voltage VE1, may be used as the first sensor output Vo1.

Then, it is determined in step S4 whether the first sensor output Vo1 is on a low electric potential side (lean side in the air-fuel ratio) with reference to a predetermined threshold output Vth (in the present embodiment, a threshold output Vth of 0.5 V). When the first sensor output Vo1 is smaller than the threshold output Vth (=0.5 V) (Yes), the procedure goes to step S5. On the other hand, in the other case, that is, when the first sensor output Vo1 is equal to or larger than the threshold output Vth (=0.5 V) (No), the procedure goes to step S6.

In step S5, the reference resistance value RTs is corrected according to the value of the first sensor output Vo1 using the first correction function fn1 expressed by the above-mentioned Formula 6 to obtain the target resistance value RT, and then the procedure goes to step S7. Here, the first inclination A1 and the first intercept B1 of the first correction function fn1 are values that are calculated and stored in step S109 of a degradation detection routine (described later). Further, the reference resistance value RTs is a value that is obtained and stored in step S108 of the degradation detection routine (also described later).

On the other hand, in step S6, the reference resistance value RTs is corrected according to the value of the first sensor output Vo1 using the second correction function fn2 expressed by the above-mentioned Formula 7 to obtain the target resistance value RT, and then the procedure goes to step S7. Here, the second inclination A2 and the second intercept B2 of the second correction function fn2 are values that are calculated and stored in step S110 of the degradation detection routine. Further, the reference resistance value RTs is the value that is obtained and stored in step S108.

In step S7, the energization control for the heater 4 is continued using the target resistance value RT obtained in step S5 or step S6 so that the internal resistance Ri detected in step S3 becomes the target resistance value RT. Thus, it is possible to appropriately perform the energization control for the heater 4 according to the degree of degradation (degradation index ID) of the detection element 3 and the difference in the gas atmosphere (the first sensor output Vo1).

In the subsequent step S8, it is determined whether there is an instruction of termination of the heater control. When there is no termination instruction (No), the procedure returns to step S1 and restarts the control program from the obtainment of the sensor output Vout. On the other hand, when there is the termination instruction, the present control program is terminated.

Figure 12:
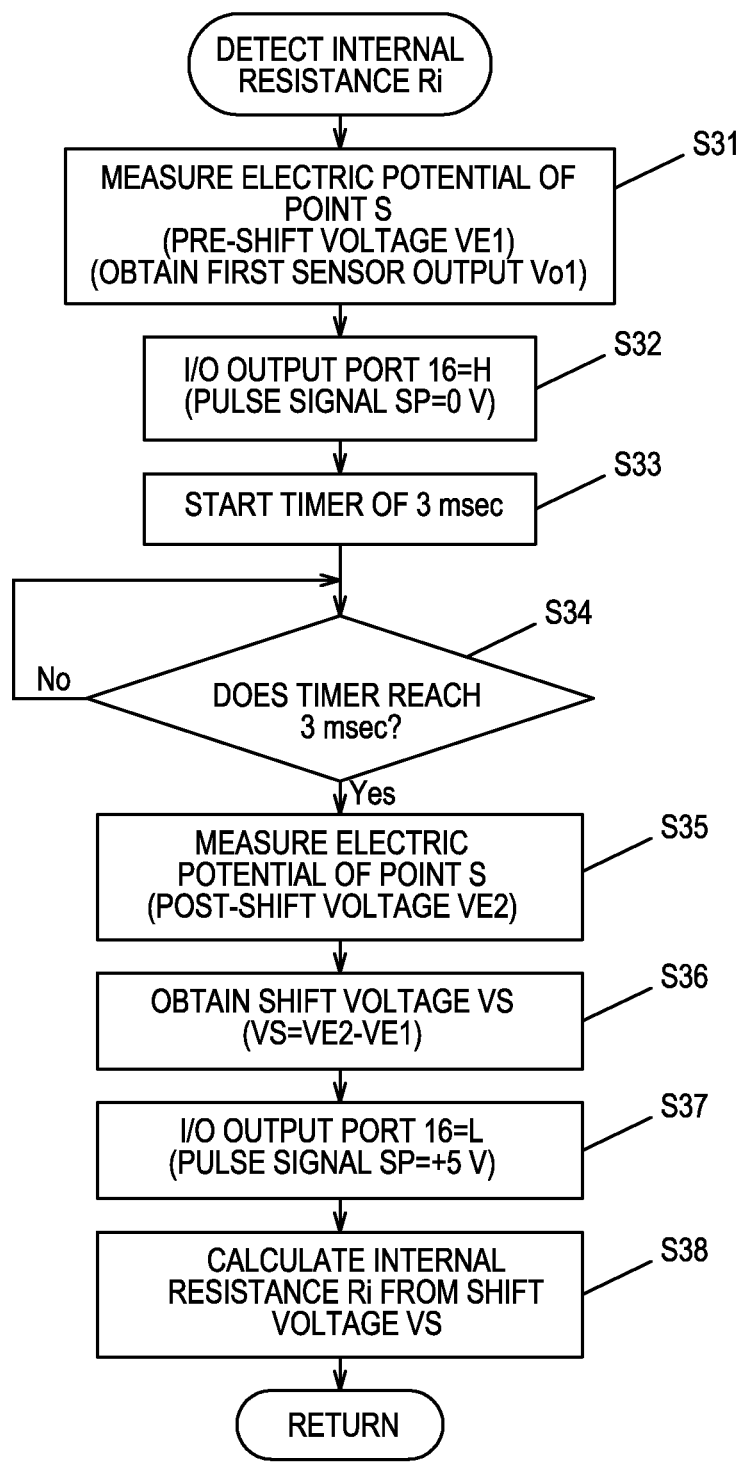
FIG. 12 is a flowchart illustrating content of an internal resistance detection routine.

Then, the internal resistance detection routine (step S3 in FIG. 11) will be described referring to the flowchart in FIG. 12. As described above, in the internal resistance detection routine, the temporary change occurs in the detection element voltage VE between the electrodes 3P and 3N of the detection element 3 to detect the internal resistance Ri.

First, in step S31, in a state where the output of the I/O output port 16 is set to the low level and the transistor Tr2 is turned off, the electric potential of the point S (accordingly, the electric potential of the point Q passed through the low pass filter circuit 15) is measured by the output detection circuit 12 through the A/D input port 17, and the result is set as the pre-shift voltage VE1 before the change occurs in the detection element voltage VE (time (a) in FIG. 3). Further, since the pre-shift voltage VE1 is the sensor output Vout (=EV) indicating the electromotive force EV depending on the oxygen concentration, the value is set as the first sensor output Vo1.

Next, the procedure goes to step S32, the output of the I/O output port 16 is switched to the high level, and the transistor Tr2 is turned on. Thereafter, the procedure goes to step S33, and a timer that counts 3 msec is started. Then, as the transistor Tr2 is turned on and the electric current I flows into the detection element 3, the voltage drop occurs in the internal resistance Ri, and the detection element voltage VE is changed.

Further, in the subsequent step S34, the procedure waits until the timer reaches 3 msec in step S33. That is, while the timer does not reach 3 msec (No), step S34 is repeated. Further, if the timer reaches 3 msec (Yes), the procedure goes to step S35.

In step S35, the electric potential (electric potential of the point Q passed through the low pass filter circuit 15) of the point S is measured by the output detection circuit 12 through the A/D port 17 again, and the result is set as the post-shift voltage VE2 in which the change occurs in the voltage detection voltage VE (time (b) in FIG. 3).

Then, the procedure goes to step S36, and the shift voltage VS is obtained from the difference between the post-shift voltage VE2 and the pre-shift voltage VE1 (VE2−VE1).

Further, the procedure goes to step S37, and the output of the I/O output port 16 is returned to the low level to turns off the transistor Tr2.

Then, the procedure goes to step S38, the internal resistance Ri is calculated using the shift voltage VS and the pre-shift voltage VE1, and then, the present internal resistance detection routine is terminated.

Figure 13:
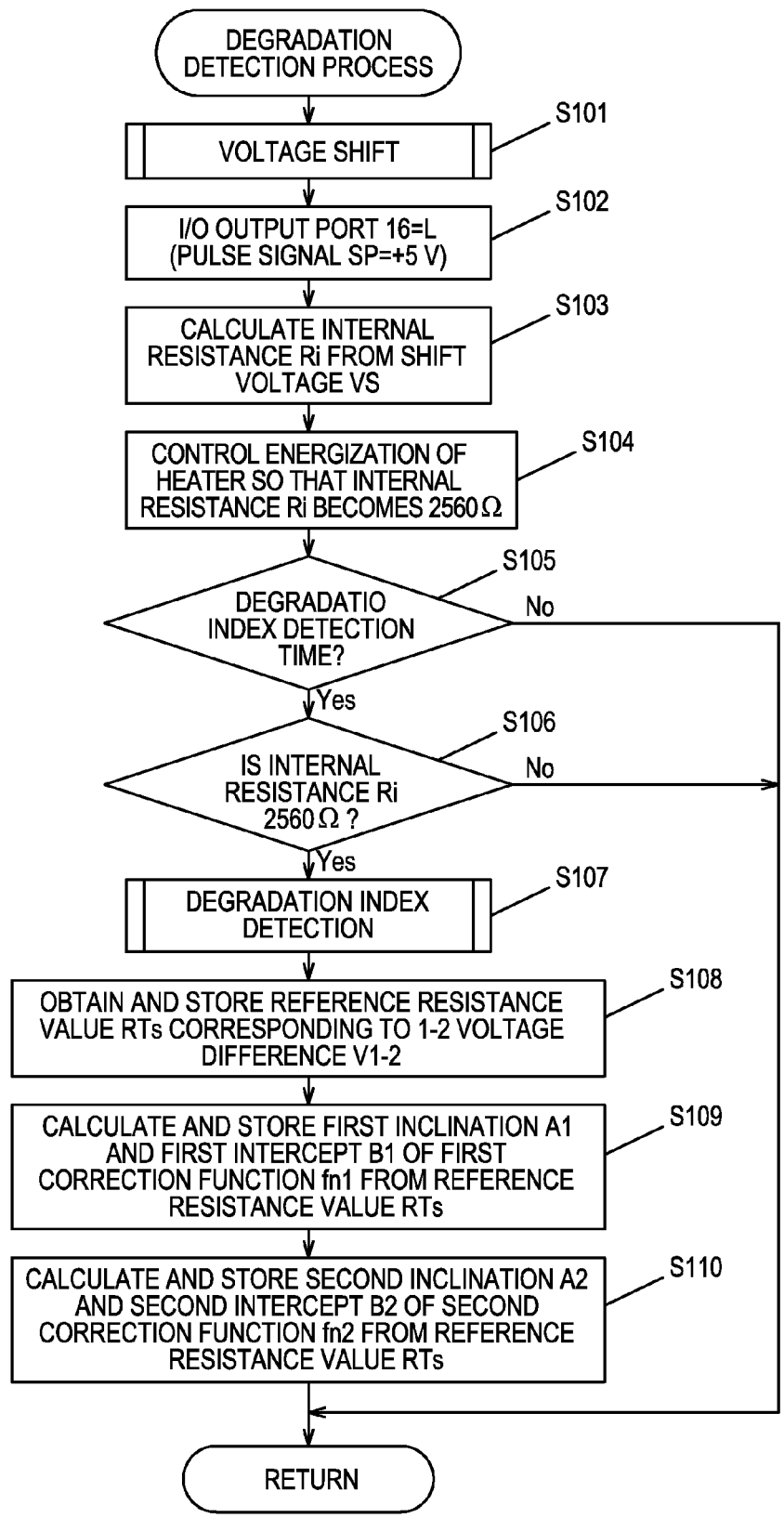
FIG. 13 is a flowchart illustrating content of a degradation detection routine.

Next, the degradation detection routine will be described referring to the flowchart in FIG. 13. In order to obtain the 1-2 voltage difference V1−2 that is the degradation index ID, the energization of the heater is temporarily stopped after the stop of the engine, and then, after a predetermined waiting time elapses, the degradation detection routine is separately executed from the control program in FIG. 11.

First, in step S101, a voltage shift sub-routine (described later) (see FIG. 14, details thereof will be described later) is executed. In the voltage shift sub-routine, a voltage shift of the detection element voltage VE is performed, and the pre-shift voltage VE1, the post-shift voltage VE2 and the shift voltage VS are obtained. Further, at the end of the voltage shift sub-routine, the output of the I/O output port 16 is set to the high level, and the point T of the output of the pulse signal output circuit 11 becomes 0 V, and thus, the transistor Tr2 is turned on.

Next, the procedure goes to step S102, and the output of the I/O output port 16 is returned to the low level. Then, the point T of the output of the pulse signal output circuit 11 becomes +5 V, and the transistor Tr2 is turned off Then, the procedure goes to step S103, and the internal resistance Ri is calculated using the shift voltage VS and the pre-shift voltage VE1 (electromotive force EV) obtained in the voltage shift sub-routine (step S101). Further, in the subsequent step S104, the energization of the heater 4 is controlled so that the obtained internal resistance Ri becomes 2560Ω. Specifically, the PWM duty ratio of the energization control of the heater is determined by the PID control or the PI control, and the PWM pulse is output from the PWM output port 18. Thus, the heater 4 is PWM-controlled and the temperature of the detection element 3 is controlled to about 400° C.

Then, in step S105, it is determined whether it is a degradation index detection time. Further, in the subsequent step S106, before the degradation index ID is detected, it is determined whether the obtained internal resistance Ri is 2560Ω. In the present embodiment, whenever the PWM duty ratio of the energization control of the heater in steps S101 to S104 is updated ten times, it is determined as one-time Yes in step S105. When it is not the degradation index detection time (No), the degradation detection routine is terminated as it is.

On the other hand, when it is the degradation index detection time (Yes), the procedure goes to step S106 and it is determined whether the internal resistance Ri is 2560Ω. In step S106, when the internal resistance Ri is not 2560Ω (No), the degradation detection routine is terminated as it is. When the determination result in step S5 or step S6 is No and the degradation detection routine is terminated (returned), the present degradation detection routine is repeatedly called at predetermined intervals until the degradation detection is completed.

On the other hand, in step S106, when it is determined that the internal resistance Ri is 2560Ω (Yes), the procedure goes to step S107, and the degradation index detection sub-routine (see FIG. 15, details thereof will be described later) that detects the 1-2 voltage difference V1−2 that is the degradation index ID is executed.

If the 1-2 voltage difference V1−2 is detected in step S107, the reference resistance value RTs corresponding to the 1-2 voltage difference V1−2 is obtained in step S108, and the obtained value is stored in a non-volatile memory.

Then, in step S109, the first inclination A1 and the first intercept B1 of the first correction function fn1 are calculated from the reference resistance value RTs using the above-mentioned Formula 1 and Formula 2, and the calculated values are stored in the non-volatile memory. Further, in the subsequent step S110, the second inclination A2 and the second intercept B2 of the second correction function fn2 are calculated from the reference resistance value RTs using the above-mentioned Formula 3 and Formula 4, and the calculated values are stored in the non-volatile memory. Then, the degradation detection routine is terminated.

Figure 14:
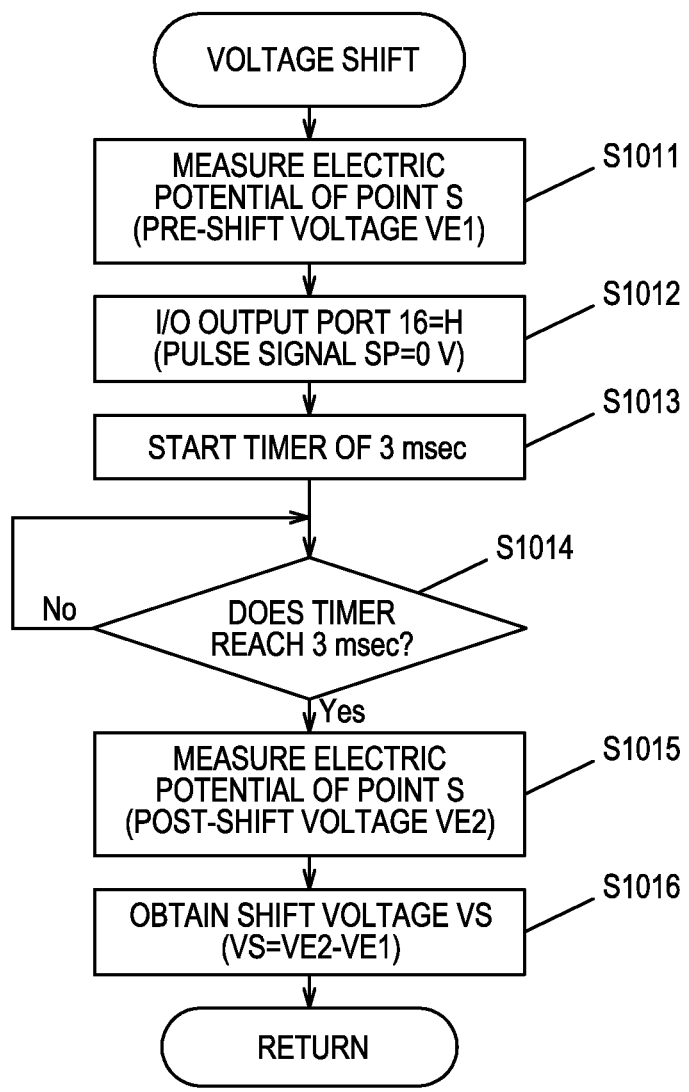
FIG. 14 is a flowchart illustrating content of a voltage shift sub-routine.

Then, the voltage shift sub-routine in step S101 will be described referring to the flowchart in FIG. 14. In the voltage shift sub-routine, as described above, the detection element voltage VE is shifted using the voltage shift circuit 19, and the pre-shift voltage VE1, the post-shift voltage VE2 and the shift voltage VS are obtained.

First, in step S1011, the microprocessor 10 measures the electric potential of the point S before voltage shift (described later) using the output detection circuit 12 through the A/D input port 17, and accordingly, measures the electric potential of the point Q (pre-shift voltage VE1) through the low pass filter circuit 15. At this time, the output of the I/O output port 16 is set to the low level, the point T of the output of the pulse signal output circuit 11 is set to +5 V, and the transistor Tr2 is turned off. Thus, the electric current does not flow into the resistor R4, and the electric potential of the point Q (and the point S) becomes a value indicating the electromotive force EV of the detection element 3. Accordingly, the value (pre-shift voltage VE1) of the electric potential of the point S (the point Q) measured in step S1011 becomes the value of the electromotive force VE (VE1=EV).

Next, the procedure goes to step S1012, and the output of the I/O output port 16 is switched to the high level. Then, the point T of the output of the pulse signal output circuit 11 becomes 0 V, and the transistor Tr2 is turned on. The time corresponds to the time point of t=0 in FIG. 2. Subsequently, the procedure goes to step S1013, and the timer that counts the time of 3 msec is started.

If the transistor Tr2 is turned on, the electric current I flows into the resistor R4, and the electric current I flows into the detection element 3. Then, the voltage drop occurs in the internal resistance Ri by the electric current I, and the electric charges are gradually accumulated in the internal capacitance Ci. Thus, the electric potential of the point Q starts from the electromotive force EV and rises as the accumulation of the electric charges to the internal capacitance Ci proceeds. In the electric potential of the point Q, the voltage relating to the rise to the electromotive force EV corresponds to a voltage between the terminals of the internal resistance Ri and the internal capacitance Ci.

In the subsequent step S1014, the procedure waits until the timer reaches 3 msec in step S1013. That is, while the timer does not reach 3 msec (No), step S1014 is repeated. Accordingly, during this period, the accumulation of the electric charges to the internal capacitance Ci proceeds, and thus, the electric potential of the point Q rises, which is close to an equilibrium state. Further, if the timer reaches 3 msec (Yes), the procedure goes to step S1015.

In step S1015, the electric potential of the point S (accordingly, the electric potential of the point Q through the low pass filter 15) is measured by the output detection circuit 12 through the A/D input port 17 again at the first detection time t1 (time t=t1=3 msec, see FIG. 2) when 3 msec elapse after the transistor Tr2 is turned on. The electric potential of the point Q reaches an approximately equilibrium state while the period (voltage shift period TS) of 3 msec elapses after the rise at the time t=0 starts (see FIG. 2), and the value at the time point of time t=t1 that is measured in step S1015 is set as the post-shift voltage VE2.

Then, the procedure goes to step S1016, the shift voltage VS is calculated as the already obtained difference (VE2−VE1) between the post-shift voltage VE2 and the pre-shift voltage VE1, and then, the voltage shift sub-routine is terminated.

Figure 15:
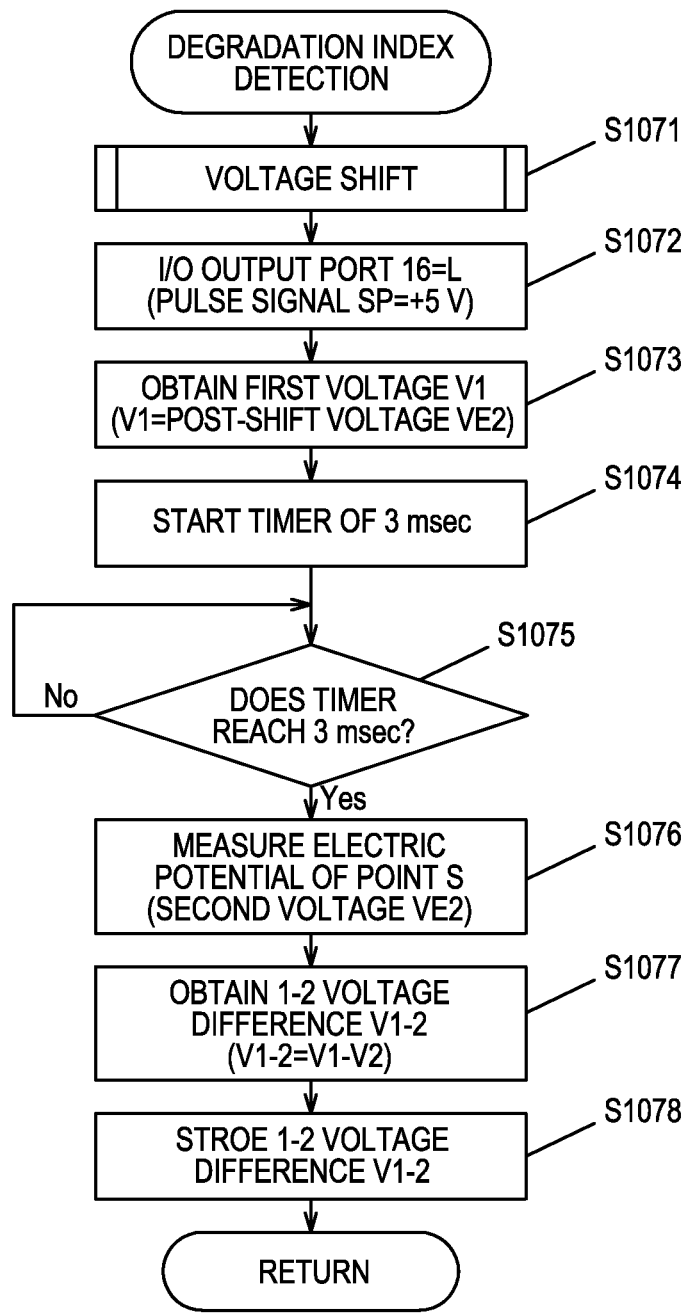
FIG. 15 is a flowchart illustrating content of a degradation index detection sub-routine.

Next, the degradation index detection sub-routine in step S107 will be described referring to the flowchart in FIG. 15. As described above, the degradation index detection sub-routine (step S107) is executed in a case where it is determined in step S106 that the internal resistance Ri of the detection element 3 is equal to 2560Ω (Yes).

First, in step S1071, the same voltage shift sub-routine as in step S101 of the degradation detection process routine is executed. At the end (at the end of step S1016) of the voltage shift sub-routine, the output of the I/O output port 16 is set to the high level, and the point T of the output of the pulse signal output circuit 11 becomes 0 V, and the transistor Tr2 is turned on.

Then, the procedure goes to step S1072, and the output of the I/O output port 16 is returned to the Low level. Then, the point T of the output of the pulse signal output circuit 11 becomes +5 V, and the transistor Tr2 is turned off. Thus, the voltage shift period TS ends, and subsequently, the recovery period TK starts.

In the subsequent step S1073, the post-shift voltage VE2 obtained in step S1015 (the first detection time t1) of the voltage shift sub-routine is obtained as the first voltage V1 (V1=VE2).

Then, the procedure goes to step S1074, and the timer that counts 3 msec is started.

Since the transistor Tr2 is turned off, an external voltage is not applied to the detection element 3 through the voltage of +5 V, and an electric current does not flow therein. Thus, the detection element 3 self-discharges the electric charges accumulated in the internal capacitance Ci through the internal resistance Ri. Thus, the electric potential of the point Q is approximately exponentially attenuated according to the time constant determined by the internal resistance Ri and the internal capacitance Ci, to thereby cause a change in the detection element voltage VE that returns to the pre-shift voltage VE1 from the post-shift voltage VE2.

In the subsequent step S1075, the procedure waits until the timer reaches 3 msec in step S1074. That is, while the timer does not reach 3 msec (No), step S1075 is repeated. Further, if the timer reaches 3 msec (Yes), the procedure goes to step S1076.

In step S1076, after the transistor Tr2 is turned off by the output detection circuit 12 through the A/D input port 17, the electric potential of the point S (the electric potential of the point Q through the low pass filter circuit 15) at the second detection time t2 (time t=t2=6 msec, see FIG. 2) when 3 msec elapse is measured. The value of the time point of time t=t2 measured in step S1076 is set as the second voltage V2.

Then, the procedure goes to step S1077, and the 1-2 voltage difference V1−2 that is the degradation index ID is calculated as the already obtained difference (V1−V2) between the first voltage V1 and the second voltage V2.

Further, the procedure goes to step S1078, and the obtained 1-2 voltage difference V1−2 is stored in the non-volatile memory, and the degradation index detection sub-routine is terminated.

As described above, in the oxygen sensor controlling apparatus 1 of the present embodiment, in order to feedback-control the energization of the heater 4, the 1-2 voltage difference V1−2 that is the degradation index ID indicating the value according to the degree of degradation of the detection element 3 is obtained at step S107. Further, using the first sensor output that is the value of the sensor output Vout immediately before the period (time (a) in FIG. 3) when the temporary change occurs in the detection element voltage VE, in addition to the degradation index ID (1-2 voltage difference V1−2), the target resistance value RT targeted by the detected internal resistance Ri is successively obtained at steps S108 to S110 and S4 to S6. That is, in order to maintain the temperature of the detection element 3 at a constant (in the present embodiment, 700° C.) target temperature, the target resistance value RT is changed according to the degree of degradation (degradation index ID) and the gas atmosphere (the first sensor output Vo1). Further, the energization of the heater 4 is feedback-controlled so that the internal resistance Ri becomes the target resistance value RT.

Thus, it is possible to appropriately control the energization of the heater 4 according to the degree of degradation of the detection element 3 (degradation index ID) and the difference in the gas atmosphere (the first sensor output Vo1) when the internal resistance Ri is detected.

Further, in the oxygen sensor controlling apparatus 1 of the present embodiment, the reference resistance value RTs corresponding to the value of the degradation index ID (the 1-2 voltage difference V1−2) is obtained at step S108, and the reference resistance value RTs is corrected according to the value of the first sensor output Vo1 at steps S109, S110, S5 and S6, to thereby obtain the target resistance value RT. Thus, it is possible to appropriately and easily obtain the target resistance value RT using the degradation index ID and the first sensor output Vo1.

Further, in the oxygen sensor controlling apparatus 1 of the present embodiment, the reference resistance value RTs is corrected using the correction function fn that uses the first sensor output Vo1 as a variable to obtain the target resistance value RT.

Accordingly, it is possible to easily obtain the target resistance value RT from the reference resistance value RTs.

Further, in the oxygen sensor controlling apparatus 1 of the present embodiment, the correction function fn is used as the composite function of the first correction function fn1 (Formula 6) that regulates a case where the first sensor output Vo1 is on the lean side with reference to the predetermined threshold output Vth and the second correction function fn2 (Formula 7) that regulates a case where the first sensor output Vo1 is on the rich side with reference to the predetermined threshold output Vth.

Accordingly, it is possible to express the correction function fn as the composite function of two simple functions (Formula 6 and Formula 7).

Further, in the oxygen sensor controlling apparatus 1 of the present embodiment, the first correction function fn1 and the second correction function fn2 are respectively expressed as the linear functions, and the first inclination A1, the first intercept B1, the second inclination A2 and the second intercept B2 thereof are given as the functions of the reference resistance values RTs, respectively.

Further, here, the first inclination A1 is set to a positive value that is increased as the degradation proceeds, and the second inclination A2 is set to a negative value of which the absolute value is increased as the degradation proceeds. Thus, the inclinations of two sides of the inverted V shape are determined Thus, it is possible to appropriately formularize the first correction function fn1 and the second correction value fn2, respectively.

Further, in the oxygen sensor controlling apparatus 1 of the present embodiment, the first inclination A1, the first intercept B1, the second inclination A2 and the second intercept B2 are given as the linear functions (Formula 1 to Formula 4) that use the natural logarithm of the reference resistance value RTs as a variable, respectively. Thus, it is possible to easily obtain the first inclination A1 and the first intercept B1 in the first correction function fn1, and the second inclination A2 and the second first intercept B2 in the second correction function fn2, from the reference resistance value RTs, respectively.

Further, in the oxygen sensor controlling apparatus 1 of the present embodiment, under the condition that the internal resistance Ri is constant (in the present embodiment, Ri=2560Ω), the value that is changed according to the change in the internal capacitance Ci depending on the degradation of the detection element 3, and specifically, the 1-2 voltage difference V1-2 is obtained as the degradation index ID. Thus, it is possible to obtain an appropriate degradation index ID.

Further, in the oxygen sensor controlling apparatus 1 of the present embodiment, the value, according to the time constant, of the change in the detection element voltage VE that is generated at the recovery period TK is obtained as the degradation index ID (voltage of the 1-2 voltage difference V1-2) at step S1071 and step S1072.

If the detection element 3 is degraded according to the degree of degradation, since a difference occurs in the time constant of the change in the detection element voltage VE at the recovery period TK, it is possible to appropriately obtain the degradation index ID indicating the value according to the degree of degradation of the detection element 3 by obtaining the value according to the time constant.

Further, in the oxygen sensor controlling apparatus 1 of the present embodiment, the voltage of the 1-2 voltage difference V1-2 is obtained as the degradation index ID.

Thus, it is possible to obtain the 1-2 voltage difference V1-2 that is easily obtained by measuring two voltages of the first voltage V1 at the first detection time t1 during the voltage shift period TS and the second voltage V1-2 at the second detection time during the recovery period TK after the voltage shift period TS ends as the degradation index ID.

Hereinbefore, the invention is described on the basis of the above-described embodiment, but the invention is not limited to the above-described embodiment, and appropriate modifications may be applied within a range without departing from the spirit of the invention.

For example, in the present embodiment, the above-mentioned 1-2 voltage difference V1-2 is obtained as the degradation index ID, but the degradation index ID is not limited thereto. For example, the detection element voltage VE generated between the electrodes 3P and 3N of the detection element 3 at the recovery period TK may be successively measured, and a time constant of an exponential function that is approximate to a change curve thereof may be obtained from the curve, to thereby use the result as the degradation index ID.

Further, in the embodiment, the voltage shift period TS is set to 3 msec, and the period from the first detection time t1 to the second detection time t2 is set to 3 msec, but these values may be appropriately selected in a range where the degradation index ID can be appropriately detected.

Further, in the present embodiment, after the engine is stopped and the predetermined waiting time elapses, the control is performed so that the internal resistance Ri is equal to 2560Ω to detect the degradation index ID, but the time when the degradation index ID is detected or the value of the internal resistance Ri at that time may be appropriately changed in a range where the degradation index ID can be appropriately detected.

Further, in the present embodiment, the first inclination A1, the first intercept B1, the second inclination A2 and the second intercept B2 are respectively provided as the linear functions that use the natural logarithm of the reference resistance value RTs as a variable on the basis of the regression formula relating to the graphs in FIGS. 7 to 10. However, the regression line may be drawn with respect to FIGS. 7 to 10, and the first inclination A1, the first intercept B1, the second inclination A2 and the second intercept B2 may be respectively provided as a linear function of the reference resistance value RTs. Further, a part of the first inclination A1, the first intercept B1, the second inclination A2 and the second intercept B2 may be provided as a linear function that uses the natural logarithm of the reference resistance value RTs as a variable, and the remaining part thereof may be provided as a linear function that uses the reference resistance value RTs as a variable.

Further, in the embodiment, when the internal resistance Ri is detected, the voltage between the electrodes 3P and 3N of the detection element 3 is temporarily changed using the pulse signal output circuit 11 and the voltage shift circuit 19 (see FIG. 1), and the variation of the voltage (shift voltage VS) due to the temporary change is obtained, to detect the internal resistance Ri. However, a configuration may be used in which by appropriately modifying the detection method of the internal resistance Ri and a circuit configuration thereof, a temporary constant current flows between the electrodes 3P and 3N of the detection element 3 to cause a voltage drop in the internal resistance Ri and a variation of the voltage due to the temporary change is obtained to detect the internal resistance Ri.

What is claimed is:
1. An oxygen sensor controlling apparatus that controls an oxygen sensor that includes: a detection element made of a solid electrolyte and having a pair of electrodes; and a heater configured to heat the detection element, in which the oxygen sensor has a characteristic that a sensor output with respect to an air-fuel ratio is changed between a rich state and a lean state with a theoretical air-fuel ratio being a boundary in response to an oxygen concentration in an exhaust gas of an internal-combustion engine, the oxygen sensor controlling apparatus comprising:
a controller configured to:
obtain a degradation index that indicates a value according to a degree of degradation of the detection element;
obtain the sensor output from the oxygen sensor;
detect an internal resistance of the detection element by causing a temporary change with respect to one of a voltage between the electrodes of the detection element and an electric current that flows between the electrodes;
successively obtain a target resistance value corresponding to the internal resistance using the degradation index and a first sensor output that is a value of the sensor output obtained at a time before or after a period when the temporary change occurs; and
feedback-control energization of the heater so that the internal resistance becomes the target resistance value,
wherein the controller is further configured to:
obtain a reference resistance value corresponding to the degradation index; and
correct the reference resistance value using a correction function that uses the first sensor output as a variable, to obtain the target resistance value, and
wherein the correction function is a composite function of:
a first correction function that regulates a case where the first sensor output is on a lean side with reference to a predetermined threshold output, with respect to the air-fuel ratio; and
a second correction function that regulates a case where the first sensor output is on a rich side with reference to the predetermined threshold output, with respect to the air-fuel ratio.

2. The oxygen sensor controlling apparatus according to claim 1, wherein
the first correction function is provided as a linear function that uses the first sensor output as a variable,
a first inclination and a first intercept that are an inclination and an intercept of the first correction function are respectively provided as a function of the reference resistance value,
the second correction function is provided as a linear function that uses the first sensor output as a variable, and
a second inclination and a second intercept that are an inclination and an intercept of the second correction function are respectively provided as a function of the reference resistance value.

3. The oxygen sensor controlling apparatus according to claim 2, wherein
the first inclination has a positive value that is increased as the degradation of the detection element proceeds, and
the second inclination has a negative value of which the absolute value is increased as the degradation of the detection element proceeds.

4. The oxygen sensor controlling apparatus according to claim 2, wherein
the first inclination, the first intercept, the second inclination and the second intercept are respectively provided as a linear function that uses the reference resistance value as a variable or a linear function that uses the natural logarithm of the reference resistance value as a variable.

5. The oxygen sensor controlling apparatus according to claim 1, wherein
the controller is configured to obtain, as the degradation index, a value that is changed according to change in an internal capacitance of the detection element depending on the degradation of the detection element, under the condition that the internal resistance is constant.

6. The oxygen sensor controlling apparatus according to claim 5, wherein
the controller is configured to:
shift the detection element voltage generated between the electrodes of the detection element from a pre-shift voltage to a post-shift voltage that is different from the pre-shift voltage;
return the detection element voltage from the post-shift voltage to the pre-shift voltage by self-discharge due to the internal resistance and the internal capacitance of the detection element, subsequent to the end of a voltage shift period in which the detection element voltage is shifted; and
obtain, as the degradation index, a value according to a time constant of change in the detection element voltage that occurs in a recovery period in which the detection element voltage is returned from the post-shift voltage to the pre-shift voltage.

7. The oxygen sensor controlling apparatus according to claim 6, wherein the controller is configured to obtain, as the degradation index, a voltage difference between a first voltage that is the detection element voltage in a first detection time in the voltage shift period and a second voltage that is the detection element voltage in a second detection time in the recovery period after the voltage shift period ends.

8. A method of controlling an oxygen sensor that includes: a detection element made of a solid electrolyte and having a pair of electrodes; and a heater configured to heat the detection element, in which the oxygen sensor has a characteristic that a sensor output with respect to an air-fuel ratio is changed between a rich state and a lean state with a theoretical air-fuel ratio being a boundary in response to an oxygen concentration in an exhaust gas of an internal-combustion engine, the method comprising:
obtaining a degradation index that indicates a value according to a degree of degradation of the detection element;
obtaining the sensor output from the oxygen sensor;
detecting an internal resistance of the detection element by causing a temporary change with respect to one of a voltage between the electrodes of the detection element and an electric current that flows between the electrodes;
successively obtaining a target resistance value corresponding to the internal resistance using the degradation index and a first sensor output that is a value of the sensor output obtained at a time before or after a period when the temporary change occurs; and
feedback-controlling energization of the heater so that the internal resistance becomes the target resistance value,
the method further comprising:
obtaining a reference resistance value corresponding to the degradation index; and
correcting the reference resistance value using a correction function that uses the first sensor output as a variable, to obtain the target resistance value, and
wherein the correction function is a composite function of:
a first correction function that regulates a case where the first sensor output is on a lean side with reference to a predetermined threshold output, with respect to the air-fuel ratio; and
a second correction function that regulates a case where the first sensor output is on a rich side with reference to the predetermined threshold output, with respect to the air-fuel ratio.

9. The method according to claim 8, wherein
the first correction function is provided as a linear function that uses the first sensor output as a variable,
a first inclination and a first intercept that are an inclination and an intercept of the first correction function are respectively provided as a function of the reference resistance value,
the second correction function is provided as a linear function that uses the first sensor output as a variable, and
a second inclination and a second intercept that are an inclination and an intercept of the second correction function are respectively provided as a function of the reference resistance value.

10. A non-transitory computer readable recording medium storing a program for an oxygen sensor controlling apparatus for an oxygen sensor that includes: a detection element made of a solid electrolyte and having a pair of electrodes; and a heater configured to heat the detection element, in which the oxygen sensor has a characteristic that a sensor output with respect to an air-fuel ratio is changed between a rich state and a lean state with a theoretical air-fuel ratio being a boundary in response to an oxygen concentration in an exhaust gas of an internal-combustion engine, the program when executed by a processor causing the oxygen sensor controlling apparatus to:
obtain a degradation index that indicates a value according to a degree of degradation of the detection element;
obtain the sensor output from the oxygen sensor;
detect an internal resistance of the detection element by causing a temporary change with respect to one of a voltage between the electrodes of the detection element and an electric current that flows between the electrodes;
successively obtain a target resistance value corresponding to the internal resistance using the degradation index and a first sensor output that is a value of the sensor output obtained at a time before or after a period when the temporary change occurs; and
feedback-control energization of the heater so that the internal resistance becomes the target resistance value,
wherein the program when executed by the processor further causing the oxygen sensor controlling apparatus to:
obtain a reference resistance value corresponding to the degradation index; and
correct the reference resistance value using a correction function that uses the first sensor output as a variable, to obtain the target resistance value, and
wherein the correction function is a composite function of:
a first correction function that regulates a case where the first sensor output is on a lean side with reference to a predetermined threshold output, with respect to the air-fuel ratio; and
a second correction function that regulates a case where the first sensor output is on a rich side with reference to the predetermined threshold output, with respect to the air-fuel ratio.

11. The non-transitory computer readable recording medium according to claim 10, wherein
the first correction function is provided as a linear function that uses the first sensor output as a variable,
a first inclination and a first intercept that are an inclination and an intercept of the first correction function are respectively provided as a function of the reference resistance value,
the second correction function is provided as a linear function that uses the first sensor output as a variable, and
a second inclination and a second intercept that are an inclination and an intercept of the second correction function are respectively provided as a function of the reference resistance value.

* * * * *